(12) United States Patent
Gascoyne et al.

(10) Patent No.: US 6,790,330 B2
(45) Date of Patent: Sep. 14, 2004

(54) SYSTEMS AND METHODS FOR CELL SUBPOPULATION ANALYSIS

(75) Inventors: Peter Gascoyne, Bellaire, TX (US); Jody V. Vykoukal, Houston, TX (US); Frederick F. Becker, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 370 days.

(21) Appl. No.: 09/883,110

(22) Filed: Jun. 14, 2001

(65) Prior Publication Data

US 2002/0036142 A1 Mar. 28, 2002

Related U.S. Application Data

(60) Provisional application No. 60/211,514, filed on Jun. 14, 2000.

(51) Int. Cl.[7] ..................... G01N 27/447; G01N 27/453
(52) U.S. Cl. ........................................ 204/547; 204/643
(58) Field of Search ............................... 204/643, 547, 204/450, 601

(56) References Cited

U.S. PATENT DOCUMENTS

| | | | |
|---|---|---|---|
| 4,001,102 A | 1/1977 | Batha et al. | 204/186 |
| 4,214,981 A * | 7/1980 | Giddings | 209/155 |

(List continued on next page.)

FOREIGN PATENT DOCUMENTS

| | | |
|---|---|---|
| EP | 0513064 | 11/1992 |
| EP | 0625267 | 11/1994 |
| EP | 0680380 | 11/1995 |
| EP | 0691891 | 1/1996 |
| EP | 0898493 | 3/1999 |
| GB | 2266153 | 10/1993 |
| JP | 1-196566 | 8/1989 |
| JP | 5-126796 | 5/1993 |
| JP | 6-18523 | 1/1994 |
| SU | 474723 | 6/1975 ................. 204/643 |
| WO | WO 90/08759 | 8/1990 |
| WO | WO 91/11262 | 8/1991 |
| WO | WO 93/16383 | 8/1993 |
| WO | WO 93/20927 | 10/1993 |
| WO | WO 94/16821 | 8/1994 |
| WO | WO 94/22583 | 10/1994 |
| WO | WO 95/13813 | 5/1995 |
| WO | WO 96/31282 | 10/1996 |
| WO | WO 97/34689 | 9/1997 |
| WO | WO 99/62622 | 12/1999 |
| WO | WO 00/69565 | 11/2000 |

OTHER PUBLICATIONS

Goater et al., "A combined travelling wave dielectrophoresis and electrorotation device: applied to the concentration of cryptosporidium," *J. Phys. D: Appl. Phys.*, 30:L65–L69, 1997, month of publication currently unknown.

"Bangor biochip heads for California," EPSRC Home Page: http://www.epsrc.ac.uk/documents/about$_{13}$ epsrc/corporate_publi . . ./ bangor.ht, article printed on Dec. 26, 2000.

(List continued on next page.)

*Primary Examiner*—Alex Noguerola
(74) *Attorney, Agent, or Firm*—Fulbright & Jaworski, LLP

(57) ABSTRACT

Systems, apparatuses and methods for cell isolation and analysis. Cells are introduced into a dielectrophoretic prefilter including one or more trapping electrodes configured to trap at least a portion of the cells with a dielectrophoretic force. The cells trapped from the prefilter are directed into a dielectrophoretic field-flow fractionation separator coupled to the prefilter. The cells are discriminated by balancing a dielectrophoretic force (and optionally a magnetophoretic force) with a gravitational force to displace the cells to positions within a velocity profile in the separator. At least a portion of the cells are trapped as a function of the cells' time of emergence from the separator with two or more spiral electrode segments coupled to the separator.

32 Claims, 9 Drawing Sheets

U.S. PATENT DOCUMENTS

| | | | |
|---|---|---|---|
| 4,326,934 A | 4/1982 | Pohl | 204/180 |
| 4,440,638 A | 4/1984 | Judy et al. | 210/198.2 |
| 5,344,535 A | 9/1994 | Betts et al. | 204/183.1 |
| 5,454,472 A | 10/1995 | Benecke et al. | 209/127.1 |
| 5,489,506 A | 2/1996 | Crane | 435/2 |
| 5,569,367 A | 10/1996 | Betts et al. | 204/547 |
| 5,571,401 A | 11/1996 | Lewis et al. | 205/787 |
| 5,653,859 A | 8/1997 | Parton et al. | 204/450 |
| 5,683,569 A | 11/1997 | Chung et al. | 205/775 |
| 5,814,200 A | 9/1998 | Pethig et al. | 204/547 |
| 5,858,192 A | 1/1999 | Becker et al. | 204/547 |
| 5,888,370 A | 3/1999 | Becker et al. | 204/643 |
| 5,965,452 A | 10/1999 | Kovacs | 436/149 |
| 5,993,630 A | 11/1999 | Becker et al. | 204/547 |
| 5,993,631 A | 11/1999 | Parton et al. | 204/547 |
| 5,993,632 A | 11/1999 | Becker et al. | 204/547 |
| 6,010,616 A | 1/2000 | Lewis et al. | 205/787 |
| 6,017,696 A | 1/2000 | Heller | 435/6 |
| 6,093,308 A | 7/2000 | Lewis et al. | 205/787 |
| 6,099,803 A | 8/2000 | Ackley et al. | 422/68.1 |
| 6,113,768 A | 9/2000 | Fuhr et al. | 204/643 |
| 6,129,828 A | 10/2000 | Sheldon, III et al. | 204/518 |
| 6,224,745 B1 | 5/2001 | Baltruschat | 205/775 |
| 6,225,059 B1 | 5/2001 | Ackley et al. | 435/6 |
| 6,287,832 B1 | 9/2001 | Becker et al. | 435/173.9 |
| 6,294,063 B1 | 9/2001 | Becker et al. | 204/450 |

OTHER PUBLICATIONS

"Diagnostic dielectrophoresis–on–a–chip," Science/Technology, 77(8):32, 1999. Article printed from http://pubs.acs.org/hotartcl/cenear/99022/7708scitobox2.html on Dec. 26, 2000.

Allsopp et al., "Impedance technique for measuring dielectrophoretic collection of microbiological particles," J. Phys. D: Appl. Phys., 32:1066–1074, 1999.

Arnold and Zimmermann, "Rotation of an isolated cell in a rotating electric field," Naturwissenschaften 69 297–300, 1982.

Balachandran et al., "Electrustatic atomization of conducting liquids using AC superimposed on DC fields," IEEE Transactions on Industry Applications, 30(4):850–854, 1994.

Becker et al., "Separation of human breast cancer cells from blood by differential dielectric affinity," Proc. Natl. Acad. Sci. USA, 92(3):860–864, 1995.

Becker et al., "The removal of human leukaemia cells from blood using interdigitated microelectrodes," J. Phys. D. Appl. Phys., 27:2659–2662, 1994.

Cheng et al., "Preparation and hybridization analysis of DNA/RNA form E. coli on microfabricated bioelectronic chips," Nature Biotechnology, 16:541–546, 1998.

Davis and Giddings, "Feasibility study of dielectrical field–flow fractionation," Separation Science and Technology, 21(9):969–989, 1986.

De Gasperis et al., "Microfluidic cell separation by 2–D dielectrophoresis," Biomedical Microdevices, 2:11, 41–49, 1999.

El–Kishky and Gorur, "Electric field and energy computation on wet insulating surfaces," IEEE Transaction on Dielectrics and Electrical Insulation, 3(4):587–593, 1996.

El–Kishky and Gorur, "Electric field computation on an insulating surface with discrete water droplets," IEEE Transaction on Dielectrics and Electrical Insulation, 3(3):450–456, 1996.

Fuller et al., "Microfabricated multi–frequency particle impedance characterization system," Micro Total Analysis System, 265–268, May 2000.

Galicki et al., "Electrohydrodynamic atomization of dielectric fluids," Conference on Electrical Insulation and Dielectric Phenomena, IEEE Annual Report, 365–368, 1996.

Gascoyne et al., "A microfluidic device combining dielectrophoresis and field flow fractionation for particle and cell discrimination," Proceedings of Solid State Sensor and Actuator Workshop, Hilton Head Supplement, 37–38, 1998.

Gascoyne et al., "Cell separation by conventional dielectrophoresis combined with field–flow–fractionation," Abstract, $40^{th}$ Annual Meeting of the Biophysical Society, Baltimore, Maryland, P. A333, Tu–Post412, Feb. 17–21, 1996.

Gascoyne et al., "Dielectrophoretic separation of cancer cells from blood," Presented at the Institute for Electrical Engineers Industrial Application Society meeting, Orlando, FL, Oct. 1995 IEEE, 1366–1373, 1995.

Gascoyne et al., "Dielectrophoretic separation of cancer cells from blood," IEEE Transactions on Industry Applications., 33(3):670–678, 1997, May/Jun.

Gascoyne et al., "Dielectrophoretic separation of mammalian cells studied by computerized image analysis," Meas. Sci. Technol., 3:439–445, 1992.

Gascoyne et al., "Manipulations of biological cells using travelling–wave dielectrophoresis," Proc. 16th IEEE: Eng. Med. Biol. Soc., 772–773, 1994.

Gascoyne et al., "Membrane changes accompanying the induced differentiation of friend murine erythroleukemia cells studied by dielectrophoresis," Biochim. Biophys. Acta, 1149:119–126, 1993.

Gascoyne et al., "Numerical analysis of the influence of experimental conditions on the accuracy of dielectric parameters derived from electrorotation measurements," Bioelectrochem. Bioenerg., 36:115–125, 1994.

Gascoyne et al., "Use of dielectrophoretic collection spectra for characterization differences between normal and cancerous cells," IEEE Trans. Ind. Appl., 30:829–834, 1994. Jul./Aug.

Gawad et al., "Impedance spectroscopy cell anaylsis in microchannels," Micro Total Analysis Systems, 253–255, 2001.

Gawad et al., "Micronarcined impedance spectroscopy flow cytometer for cell analysis and particle sizing," Lab on a Chip, 1:76–82, 2001.

Giddings, "Field–flow fractionation: analysis of macromolecular, colloidal, and particulate materials," Science, 260;1456–1465, 1993. Jun.

Hagendorn et al., "Travelling–wave dielectrophoresis of microparticles," Electrophoresis, 13:49–54, 1992.

He et al., "Droplet charge–to–mass ratio measurement in an EHD liquid–liquid extraction system," IEEE Transactions on Industry Applications, 32(1):146–154, 1996. Jan./Feb.

Higashiyama et al., "Behavior of water droplets located on a hydrophobic insulating plate under DC field," IEEE, 1808–1813, 1998.

Hoffman and Britt, "Flow–system measurement of a cell impedance properties," J. Histochemistry and Cytochemistry, 27:234–240, 1979.

Hoffman et al., "Flow cytometric electronic direct current volume and radiofrequency impedance measurments of single cells and particles," Cytometry, 1:377–384, 1981.

Hölzel and Lamprecht, "Dielectric properties of yeast cells as determined by electrorotation," Biochem. Biophys. Acta 1104:195–200, 1992.

Hoskawa et al., "Handling of picoliter liquid samples in a Poly(dimethylsiloxane)–based microfluidic device," *Anal. Chem.*, 71:4781–4785, 1999. Oct.

Huang et al., "Application of AC electrokinetics for cell characterization and manipulation," *Abstract*, 40th Annual Meeting of the Biophysical Society, Baltimore, Maryland, P. A334, Tu–Pos413, Feb. 17–21, 1996.

Huang et al., "Difference in the AC elctrodynamics of viable and non–viable yeast cells determined through combined dielectrophoresis and electrorotation studies," *Phys. Med. Biol.*, 37(7):1499–1517, 1992.

Huang et al., "Electrokinetic behaviour of colloidal particles in traveling electric fields: studies using yeast cells," *J. Phys. D: Appl. Phys.* 26:1528–1535, 1993.

Huang et al., "Electrorotational studies of the cytoplasmic dielectric properties of Friend murine erythroleukaemia cells," *Phys. Med. Biol.*, 40:1789–1806, 1995.

Huang et al., "Introducing dielectrophoresis as a new force for field–flow fractionation," *Biophys. J.*, 73:1118–1129, 1997. Aug.

Huang et al., "The removal of human breast cancer cells from hematopoietic CD34+ stem cells by dielectrophoretic field–flow–fractionation," *J. of Hemototherapy & Stem Cell Research*, 8(5):481–490, 1999.

Huneiti et al., "Harmonic spraying of conducting liquids employing AC–DC electric fields," *IEEE Transactions on Industry Applications*, 34(2):279–285, 1998. Mar./Apr.

Jinsart et al., "Inhibition if myosin light chain kinase, cAMP–dependent protein kinase, protein kinase C and of plant CA–dependent protein kinase by antraquinones," *Biological Chemistry*, 373:903–910, 1992.

Jones and Kallio, 'Dielectrophoretic levitation of spheres and shells,' *J. Electrostat.*, 6:207–224, 1979.

Jones, Electromechanics of Particles, Cambridge University Press, Cambridge, Chapter 3:34–82, 1995.

Kashyap and Gratzl, "Electrochemistry in microscopic domains. 1. The electrochemical cell and its voltammetric and amperometric response," *Anal Chem.*, 70:1468–1476, 1998. Apr.

Kloes and Koenig, "Basic investigation of the performance of droplets on electrically stressed polymer surfaces," *Conference on Electrical Insulation and Dielectric Phenomena*, IEEE Annual Report, 374–377, 1997.

Lee and Kim, "Liquid micromotor driven by continuous electrowetting," *IEEE*, 538–543,1998.

Markx and Pethig, "Dielectrophoretic separation of cells: continuous separation," *Biotechnology and Bioengineering*, 45:337–343, 1995.

Markx et al., "Dielectrophorectic characterization and separation of mirco–organisms," *Microbiol.*, 140:585–591, 1994.

Massey, "Mechanics of Fluids," $2^{nd}$ Edition, 136–139, 1975.

Metwally, "Electrostatic charging and modeling of aqueous sprays and fission of droplets," *Conference on Electrical Insulation and Dielectric Phenomena*, IEEE Annual Report, 117–120, 1996.

Mizuno et al., "Behavior of water droplets on silicone rubber sheet under AC voltage application," *IEEE*, 96–99, 1998.

Moesner et al., "Electrostatic devices for particle microhandling," *IEEE Transactions on Industry Applications*, 35(3):530–536, 1999.

Sathuvalli and Bayazitoglu, "The lorentz force on an electrically conducting sphere in an alternating magnetic field," *IEEE Transactions on Magnetics*, 32(2):386–399, 1996.

Sato et al., "Experimental investigation of droplet formation mechanisms by electrostatic dispersion in a liquid–liquid system," *IEEE Transactions on Industry Applications*, 33(6):1527–1534, 1997.

Sato et al., "Production of oil/water type uniformly sized droplets using a convergent AC electric field," *IEEE Transactions on Industry Applications*, 32(1):138–145, 1996.

Vennard, "Elementary Fluid Mechanics," 150–155, 1954. $3^{rd}$ed. John Wiley & Sons.

Wang et al., "A theoretical method of electrical field analysis for dielectrophoretic electrode arrays using Green's theorum," *J. Phys. D: Appl. Phys.*, 29:1649–1660, 1996.

Wang et al., "A Unified theory of dielectrophoresis and traveling wave dielectrophoresis," *J. Phys. D: Appl. Phys.*, 27:1571–1574, 1994.

Wang et al., "Changes in a Friend murine erythroleukaemia cell membranes during induced differentiation determined by electrorotation," *Biochimica et Biophysica Acta*, 1193:330–334, 1994.

Wang et al., "Dielectrophoretic manipulation of cells using spiral electrode arrays," *Abstract*, $40^{th}$ Annual Meeting of the Biophysical Society, Baltimore, Maryland, p. A333, Tu–Pos411, Feb. 17–21, 1996.

Wang et al., "Dielectophoretic manipulation of cells with spiral electrodes," *Biophys. J.*, 72:1887–1899, 1997.

Wang et al., "Dielectrophoretic manipulation of particles," presented at the instituted for electrical engineers industrial application society meeting, Orlando, FL, Oct. 1995.

Wang et al., "Non–uniform spatial distributions of both the magnitude and phase of AC electric fields determine dielectrophoretic forces," *Biochem. Biophys. Acta*, 1243(2):185–194, 1994.

Wang et al., "Particle dipole–dipole interactions in AC electric fields," *Proc. $16^{th}$ IEEE: Eng. Med. Biol. Soc.*, 774–775, 1994.

Wang et al., "Relationship of dielectrophoretic and electrorotational behaviour exhibited by polarized particles," *J. Phys. D: Appl. Phys.*, 25:905–912, 1992.

Wang et al., "Separation of polystyrene microbeads using dielectrophorecti/gravitational field–flow–fractionation," *Biophysical Journal*, 74:2689–2701, 1998.

Washizu et al., "Molecular dielectrophorcsis of biopolymers," *IEEE Trans on Industry App.*, 30(4):835–843, 1994. Jul./Aug.

Washizu, "Eletrostatic actuation of liquid droplets for microreactor applications," *IEEE Transactions on Industry Applications*, 34(4):732–737, 1998.

Yang et al., "Cell separation on mircofabricated electrodes using dielectrophoretic/gravitational field–flow fractionation," *Analytical Chem.*, 71(5): 911–918, 1999. Mar.

Yeh et al., "Effects of antraquinones of Polygonum cuspidatum on HL–60 cells," *Planta Medica*, 54:413–414, 1988.

Zborowski et al., "Continuous cell separation using novel magnetic quadrupole flow sorter," *J. Mag. & Mag. Materials*, 194:224–230, 1999.

Zhang et al., "Sensitization of HER–2/Neu overexpressing non–small cell lung cancer cells to chemotherapeutic drugs by tyrosine kinase inhibitor emodin," *Oncogene*, 12:571–576, 1996.

Zhang et al., "Suppressed transformation and induced differentiation of HER–2/Neu overexpressing breast cancer cells by emodin," *Cancer Res.*, 55:3890–3896, 1995. Sep.

Co–pending U.S. patent application Ser. No. 09/882,805, by Peter R.C. Gascoyne et al., filed Jun. 14, 2001.

\* cited by examiner

Separation Summary

| Experiment Parameters | Cell Types | Ratio (before) | Purity (after) | Separation Time (min) |
|---|---|---|---|---|
| 15-40 kHz, 5 min; 5 kHz, 7 min | MDA435 CD34+ Cells | 2 : 3 | 99% 99.2% | 12 |
| 5 kHz, 30 min | MDA435 Erythrocytes | 1 : 1 | 99.9% 99.9% | 30 |
| 15-35 kHz, 5 min; 5 kHz, 7 min) | MDA435 T-lymphocytes | 2 : 3 | 98% 92% | 12 |
| 20-50 kHz, 10 min; 5 kHz, 6 min | Monocytes T-lymphocytes | 1 : 1 | 98% 92% | 16 |
| 20-40 kHz, 10 min; 5 kHz, 6 min | Monocytes B-lymphocytes | 1 : 1 | 94% 92% | 16 |
| 40-50 kHz, 8 min; 5 kHz, 5 min | Granulocytes T-lymphocytes | 1 : 1 | 94% 87% | 13 |
| 30-35 kHz, 8 min; 5 kHz, 5 min | Monocytes Granulocytes | 1 : 1 | 97% 91% | 13 |
| 40-55 kHz, 5 min; 25-35 kHz 5 min; 5 kHz, 5 min | T-lymphocytes Granulocytes Monocytes | 8 : 8 : 1 | 96% 91% 58% | 14 |
| 10 kHz, 25 min | Leukocytes Erythrocytes | 1 : 700 | 5% 99.99% | 25 |

FIG. 4

SYSTEMS AND METHODS FOR CELL SUBPOPULATION ANALYSIS

This application claims the benefit of U.S. Provisional Application No. 60/211,514, filed Jun. 14, 2000.

BACKGROUND OF THE INVENTION

1. Field of the Invention

The present invention relates generally to fluidic processing and, more particularly, to methods and apparatuses concerning an integrated fluidic device capable of enriching and isolating a suspect cell subpopulation from a suspension of cells and quantitatively analyzing that subpopulation for marker proteins and mRNAs for the purpose of detection and diagnosis of conditions such as cancer.

2. Description of Related Art

The identification of increasing numbers of genes that influence disease states and the approach of the post-genomic era make evident the need for faster and automated technologies that will allow dissemination of the gains of molecular diagnosis. If sufficiently small, automatic and inexpensive devices can be developed for molecular screening, they would not only revolutionize the diagnosis and prognosis of cancer and other diseases but also would enable molecular methods to be disseminated completely—even to the point of care.

Although some devices such as gene chips and chip embodiments of the polymerase chain reaction (PCR) are beginning to enter use, many of the methods developed so far are labor intensive and are not readily suited to automated, continuous monitoring, or high throughput applications. Clearly, a wide range of enabling technologies is needed before integrated instruments capable of automated sample preparation and molecular analysis of clinical samples become a reality.

SUMMARY OF THE INVENTION

Technology that is the subject of the present addresses issues related to the creation of multiple-use diagnostic systems for combined sample preparation and detection of molecular markers. Disclosed herein are systems, methods, and devices capable of performing fully automated assays. These devices offer the advantages of small size, low sample volume requirements, and the potential for mass production at low cost. Such low-cost systems are applicable to reusable or disposable medical devices.

In one embodiment, such a system may include the following subsystems: (1) a prefilter stage to concentrate suspect cells; (2) a high discrimination separator stage to fractionate cell subpopulations; (3) a stage to burst cells and mobilize molecular components; and (4) a stage for automated analysis of protein and mRNA molecular diagnostic markers.

Important technologies for the development of such a system, and others made apparent by the present disclosure include the following: a prefiltering methodology to trap suspected cancer cells from blood or dispersed lymph node cells; a force balance method that exploits dielectric properties of the suspect cells, and, if needed, their immunomagnetic labeling properties, to fractionate them into a microfluidic isolation and analysis chamber; and a dielectric indexing and manipulation method for carrier beads that, when combined with certain established molecular assay methods, allows for the parallel quantification of multiple molecular markers.

As certain technology disclosed herein builds upon work involving dielectrophoretic trapping, dielectrophoretic field-flow fractionation (DEP-FFF), traveling wave methods, and other work performed by the inventors, the following are hereby specifically incorporated by reference herein in their entirety: U.S. Pat. No. 5,993,630 entitled "Method and Apparatus for Fractionation Using Conventional Dielectrophoresis and Field Flow Fractionation"; U.S. Pat. No. 5,858,192 entitled "Method and Apparatus for Manipulation Using Spiral Electrodes"; U.S. Pat. No. 5,888,370 entitled "Method and Apparatus for Fractionation Using Generalized Dielectrophoresis and Field Flow Fractionation"; U.S. Pat. No. 5,993,632 entitled "Method and Apparatus for Fractionation Using Generalized Dielectrophoresis and Field Flow Fractionation"; U.S. application Ser. No. 09/249,955 filed Feb. 12, 1999 and entitled "Method and Apparatus for Programmable Fluidic Processing" now U.S. Pat. No. 6,294,063; U.S. application Ser. No. 09/395,890 filed Sep. 14, 1999 and entitled "Method and Apparatus for Fractionation Using Generalized Dielectrophoresis and Field Flow Fractionation", now U.S. Pat. No. 6,287,832; U.S. Provisional Application No. 60/211,757 filed Jun. 14, 2000 and entitled "Method and Apparatus for Combined Magnetophoretic and Dielectrophoretic Manipulation of Analyte Mixtures"; U.S. Provisional Application No. 60/211,515 filed Jun. 14, 2000 and entitled "Dielectrically-Engineered Microparticles"; U.S. Provisional Application No. 60/211,516 filed Jun. 14, 2000 and entitled "Apparatus and Method for Fluid Injection."

Dielectric indexing represents a new approach to identifying individual molecular tests in a parallel molecular analysis scheme that substitutes dielectric indexing of carrier beads for the spatial indexing used on a gene chip. This new approach allows different subpopulations of beads, each carrying a probe of a different molecular marker, to be identified and manipulated within the carrier medium using a dielectric fingerprint unique to each bead/probe type. The need to immobilize different molecular probes in a tightly specified pattern on a fixed substrate as demanded, for example, by gene chip technology, is thereby eliminated. Mixtures of probes, each probe carried on a separately indexed bead type, may be injected into and flushed from a reusable assay system in order to examine any desired panel of molecular markers.

The use of bead dielectric properties as an indexing parameter not only provides the capability of manipulating beads through dielectrophoresis or another suitable manipulation force, but also offers a new alternative to optical or fluorescent bead indexing methods that might interfere with low light emissions in fluorescent probe assays.

Technology disclosed herein builds upon and synthesizes aspects of many disciplines including field-flow fractionation (physical chemistry), dielectrophoresis and magnetophoresis (physics), microfluidics (mechanical and fluid engineering), microfabrication (photolithography, MEMS and magnetic materials science), control electronics (electrical engineering), antibody and nucleic acid binding and linking (immunology and molecular biology), cell biology (cell culture and cytology), flow cytometry, and oncology.

BRIEF DESCRIPTION OF THE DRAWINGS

The following drawings form part of the present specification and are included by way of example and not limitation to further demonstrate certain aspects of the present invention. The invention may be better understood by reference to one or more of these drawings, in which like references indicate similar elements, in combination with the detailed description of specific embodiments presented herein.

FIG. 4 is a chart summarizing DEP-FFF separation data for various cell types.

DESCRIPTION OF ILLUSTRATIVE EMBODIMENTS

Figure 1:
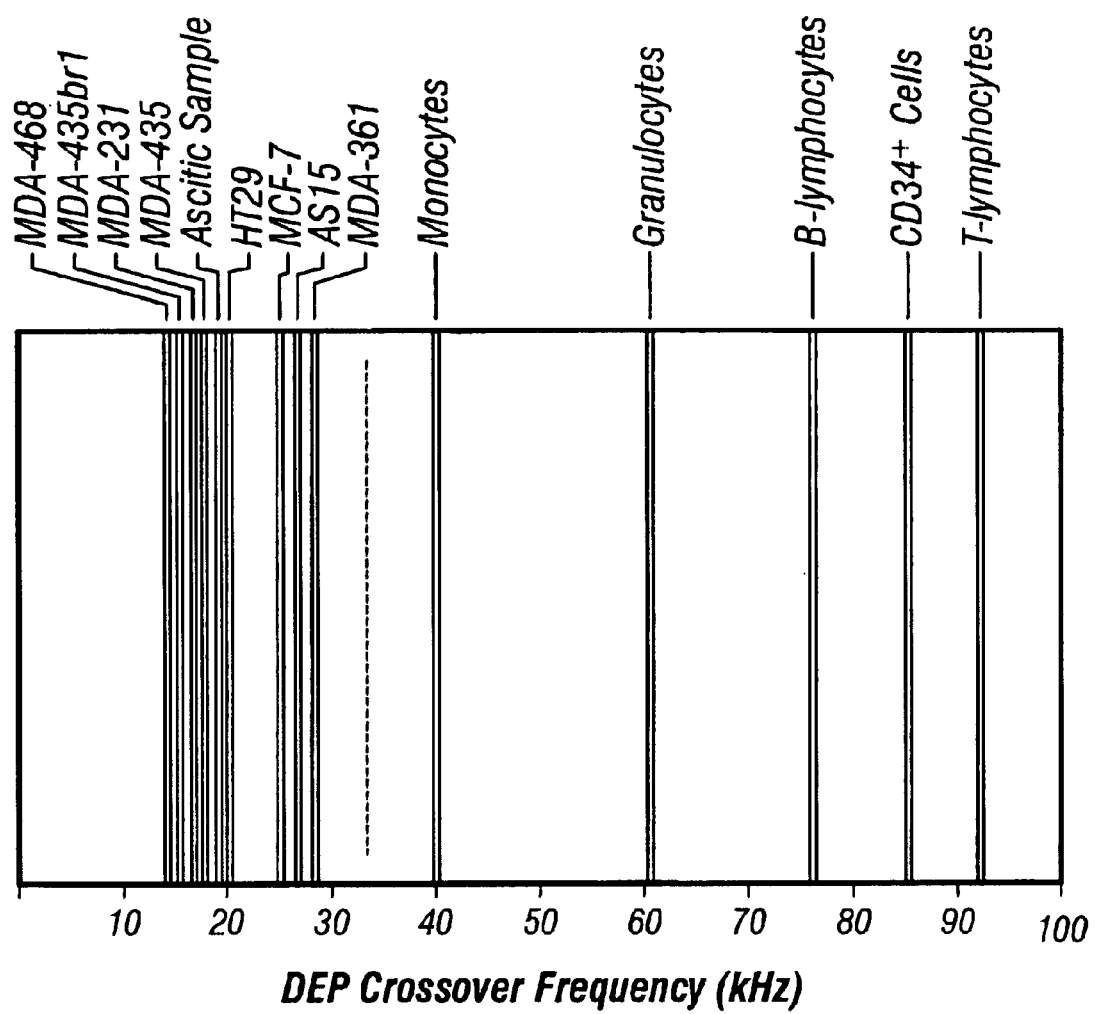
FIG. 1 is graph showing different DEP crossover frequencies. It compares the crossover frequencies for nine human tumor cell types and normal peripheral blood mononuclear cells.

The presently disclosed systems, methods and apparatuses provide many advantages (a few of which are the following). They permit for cell pre-filtering that may be used to separate tumor cells from peripheral blood mononuclear cells (PBMNCs). They allow for Dielectrophoretic-magnetophoretic field-flow fractionation (DEP-MAP-FFF), allowing for combined dielectrophoretic and immunomagnetic cell separation. They allow for the dielectric indexing of beads, the linkage of antibody and oligonucleotide probes to bead surfaces, and for the simultaneous assays for two molecular markers using a mixture of two different bead/probe types. They allow for the quantification of the association of targets with the beads and identifications of the bead types by dielectric measurements using impedance sensing methods. They allow for DEP-MAP-FFF fractionation of cells according to their surface receptor concentrations. They allow for DEP focusing of samples using swept frequency traveling fields applied to spiral electrode arrays that can be used to concentrate isolated cell fractions to ~109 cells/ml. They allow for the electro-mediated bursting of cells. They also allow for the mixtures of different bead/probe combinations to be used to perform parallel assays with dielectric indexing.

Areas that may benefit from this technology include, but are not limited to: blood and urine assays, pathogen detection, pollution monitoring, water monitoring, fertilizer analysis, the detection of chemical and biological warfare agents, food pathogen detection, quality control and blending, massively parallel molecular biological protocols, genetic engineering, oncogene detection, and pharmaceutical development and testing.

Because the present disclosure deals, in part, with the combination of a number of technologies that may be discussed separately, it is useful to begin the discussion with some theoretical underpinnings and considerations relating to some of the individual techniques disclosed herein. In the Examples section, discussion will focus more upon the combination of the techniques to form systems and apparatuses (and associated methodology) according to embodiments of this disclosure.

Certain techniques of this disclosure use molecular recognition and sensing elements that are attached to bead carriers so that a new aliquot of sensitized beads can be used for each and every assay. By disposing of the beads afterwards, by running a "blank" between each sample, and by allowing for cleaning cycles, calibration issues can be addressed and the absence of carryover and cross-contamination can be verified.

Placing biologically active components on beads also means that a single, fluidic device may be applied to a wide range of sample preparation and molecular analysis problems by using different bead/probe combinations. Finally, because no biological components need be attached to fixed surfaces within the device of one embodiment, those surfaces may be PTFE coated, for example, to reduce biomolecular adhesion and carryover issues. It follows that the use of beads enhances the potential applicability of the technology by allowing a single device to have multiple applications.

Although molecular amplification techniques enjoy widespread use, methods such as PCR have drawbacks including sensitivities to hard-to-control factors that can render them only marginally quantitative. Furthermore, molecular amplification bathes the reaction surfaces with high concentrations of the molecules to be detected. The resultant carryover problem is so severe that all wetted surfaces in molecular amplification experiments are typically made disposable. For these reasons, this disclosure avoids direct molecular amplification steps in designing reusable devices and focuses on detecting small numbers of molecules trapped directly on beads. Nevertheless, having the benefit of this disclosure, those having skill in the art recognize that the bead-based indexing technology described here is also compatible with molecular amplification protocols should they be required.

Any in-situ hybridization assay may be adapted to operate on the surface of a carrier bead including methods for detecting DNA, RNA and proteins. In this disclosure, the established body of hybridization and immuno-fluorescent molecular techniques may be used along with new methods for indexing bead carriers so that individual bead types within a complex mixture of bead types are identifiable, amenable to selective manipulation, and, if desired, to isolation. Assays using dielectrically-engineered beads require minimal quantities of sample. For example, a bead of about 5 $\mu$m diameter has the relatively large surface area of approximately 78 $\mu m^2$ yet occupies a volume of only 65 fL, about ¹/₁₅ that of a typical tumor cell. 100 tumor cells and 250 beads comprised of 10 different bead types may be packed into spherical region of 50 μm diameter using DEP-mediated focusing. This is the equivalent of almost $10^9$ cells/ml held in contact with $2\times10^9$ beads/ml carrying the molecular probes. The time for hybridization of target mRNA's to cDNA probes on magnetic bead surfaces has been shown to be just a few minutes in concentrated cell lysates; therefore, the bead-based approach of this disclosure may enable rapid assays for molecular markers in an integrated system.

The bead-based, dielectric indexing technology of this disclosure is not meant to replace large gene-chip array methods designed for massively parallel analysis of the expression of 10,000 or more genes. Those methods permit the identification, in the first place, of key markers of specific cellular events. Instead, this disclosure represents a technology in which a reduced panel of 10 or so key molecular markers may be selected from a library of available markers for the purpose of screening for specific subsets of suspected disease states. By combining sample preparation and molecular analysis into a single, automated process, this system allows the exploitation of gene-chip-derived molecular epidemiological data and renders it accessible to a wide population.

This disclosure addresses the isolation of suspect cells from mixed cell suspensions and the manipulation of mixtures of dielectrically indexed beads, all in an integrated device. Achieving these steps ultimately depends upon ways of moving matter with respect to the solution that suspends it, a problem to which dielectrophoresis, or another suitable manipulation force, is ideally suited.

Dielectrophoresis (DEP) is the movement of a material or an object caused by a spatially non-uniform electrical field. Completely distinct from the well-known phenomenon of electrophoresis, DEP only arises when the object has a different tendency to become electrically polarized relative to its surroundings. If the object is more polarizable than its surroundings, it will be pulled-towards higher field regions ("positive DEP"); conversely it will be repelled towards weak field regions ("negative DEP") if it is less polarizable. Positive DEP is known to most of us as the attraction of uncharged bits of paper to a charged plastic comb. Magnetophoresis is the magnetic analog of dielectrophoresis, the collection of magnetically polarizable particles in a spatially non-uniform magnetic field. This force is responsible for the familiar collection of iron filings at the fringing fields at the edges of a magnetic pole. Far from being restricted to electrostatic fields, DEP also occurs in alternating (AC) fields even at optical frequencies. An example is when a laser tweezers is used to trap a cell having a higher refractive index (larger electronic polarizability) than its suspending medium at the high field gradient focal region of the laser beam. (There is also a second, light pressure term in this extreme case). At lower frequencies DEP can be used to impose forces on cells that depend on their low-frequency spectral properties. Differences in these spectral properties can be exploited to impose different or even opposing forces on different cell types in a cell mixture. For techniques of this disclosure, relatively low frequencies may be used, from about 10 kHz to about 10 MHz, at which cell membrane and bead coating properties dominate the particle dielectric properties.

The essential characteristic of DEP is the movement of objects with respect to their suspending medium. For example, objects can be concentrated to a focal point by negative DEP and/or trapped by positive DEP. In addition, different particle types can be moved apart from one another in three dimensions under appropriate field conditions. These basic manipulations can be used to sort, isolate, and trap cells and beads, and to change the reagents in which they are suspended.

Of particular relevance to this disclosure is the extensive DEP work on normal and cancer cells in which the inventors and others have shown that different cell types have distinct dielectrophoretic fingerprints and may be used (in accordance with embodiments disclosed herein) to characterize, manipulate, fractionate, isolate, trap, and selectively burst them.

Summarizing, DEP is a force that:
1. arises when a particle having dielectric properties distinct from its carrier medium is subjected to a spatially non-uniform electrical field anywhere from DC to optical frequencies;
2. in complete contrast to electrophoresis, completely ignores any net charge on the particle (this is a critical consideration when performing assays with highly charged biomolecules such as nucleic acids);
3. can be used to trap, focus, fractionate and isolate cells;
4. depends specifically on the dielectric fingerprint of each cell type. In principle, DEP can be used to exploit any spectral differences between cells but this disclosure focuses on low frequency differences dominated by plasma membrane morphological characteristics;
5. can be produced by an AC electrical field that typically has a frequency between 10 kHz and 1 MHz for cell isolation experiments. No electrolysis occurs at these frequencies and cells are not damaged unless the field is deliberately increased above a high threshold magnitude to achieve controlled cell bursting;
6. can be produced by an array of micro electrodes that are inexpensive to fabricate according to methods known in the art;
7. can be produced at AC frequencies even if the electrodes carry a thin coating of PTFE or other insulator;
8. is controlled via the frequency and/or voltage of the signal applied to the electrodes. The electronics are straightforward, can be incorporated in a box the size of a pocket calculator, are inexpensive, and can be kept separate as is all known in the art so that DEP chambers may be disposable while the electronics are retained;
9. is ideal for meso- and microfluidic-scale applications because electrodes can line the floor and/or walls of fluidic channels and chambers;
10. allows cells, beads, or other targets to be selectively manipulated within their carrier medium or held in place while a new carrier medium is washed over them.

In one embodiment, high discrimination sample preparation of suspect tumor subpopulations is accomplished through a separation technique called hyperlayer field-flow fractionation. The underlying principle is straightforward: the velocity of fluid flowing through a flat channel increases from zero at the floor and ceiling to a maximum at the center. If different cell types are positioned at different characteristic heights above the channel floor then they will be carried at different velocities by the fluid and separated as the cell mixture travels through the channel. The different types can then be isolated and trapped as they emerge from the far end of the channel. Separation does not depend on the interaction of cells with any material other than the carrier fluid, reducing non-specific binding, carryover, and contamination effects that are inherent in chromatographic methods, for example.

To position different cell types characteristically in the separation channel, one may balance dielectrophoretic and gravitational forces on cells. Additionally, magnetophoretic forces may be used as well for positioning cells if desired. In this way, immunomagnetic labeling can be used as an additional feature to discriminate between different cell types. The DEP-MAP-FFF method is equally applicable to cells, which have their own intrinsic dielectric properties, and to beads that can act as molecular marker carriers. When a cell subpopulation has intrinsic dielectric differences that distinguish if from other cell types in a mixture, it is not necessary to use magnetic labeling and the method may revert to a DEP-FFF scheme.

The continuous MAP-sorting of immunomagnetically labeled cells in a laminar flow profile subjected to a quadrupole magnetic field configuration has been demonstrated. While the sorting of cells according to surface receptor density was achieved, the method has the disadvantage that the MAP force is unbalanced.

Consequently, separation is flow-rate dependent. Furthermore, heavily labeled cells may collide with the sides of the flow chamber only to become trapped or to suffer remixing with other cell types. The DEP-MAP-FFF design of the present disclosure, however, balances opposing DEP and MAP forces to place cells in equilibrium positions in the flow profile. In this way, the pitfalls of unbalanced forces, which are likely to be of even greater concern when sorting inherently inhomogeneous tumor cell subpopulations, may be avoided.

In addition to cell sorting, DEP may be used to prefilter cells when large numbers of cells need to be processed, to trap cells after they emerge from the DEP-MAP-FFF separator, to concentrate the cell isolates and beads, to lyse the cells, and to hold beads in place while reagents are changed in molecular analysis protocols. In this way, dielectrophoresis provides for the ability to realize an automated device that will integrated a sample prefilter, a DEP-MAP-FFF separator, a cell fraction isolation and lysis stage, and a molecular analysis stage.

Sample Preconcentration

In one embodiment, a DEP-MAP-FFF system may take a sample of about 20 $\mu L$ of cell suspension containing a maximum of $2 \times 10^5$ cells when performing high resolution separations. A lower detection limit of 20 cancer cells in the molecular analysis stage requires an incidence of 1 or more cancer cells per 1000 normal cells. While this level of discrimination is adequate for biopsy samples of putatively tumorous tissue, in other applications, such as the detection of residual disease, of metastatic cells in bone marrow harvests, or of micrometastases in sentinel lymph nodes, the goal is to detect 1 tumor cell per $10^6$ or more normal nucleated cells. To provide 20 tumor cells for analysis in such applications, there is the need to sort $>2 \times 10^7$ normal cells, a number that far exceeds the capacity of DEP-MAP-FFF separator stage because to achieve high discrimination this stage needs to operate at cell concentrations where cell—cell interactions are negligible.

To sort high numbers of cells, a stage that will execute a DEP prefiltering step for suspect cancer cells may therefore be needed. While prefiltering does not provide a pure population of suspect cells, it does provide a sample that is suitable for the DEP-MAP-FFF stage of the device (which is explained and illustrated, in one embodiment, in the Examples section of this disclosure). In one embodiment, the prefilter may process $\sim 20 \times 10^6$ cells and extract $\sim 2 \times 10^5$ cells enriched in the suspect cell subpopulation. Those $2 \times 10^5$ cells may then be routed to a high discrimination DEP-MAP-FFF separator stage. If the lower limit of molecular analysis in the last stage of the integrated device is 20 cancer cells, then the integrated device may achieve a detection limit of 1 cancer cell per $10^6$ starting nucleated cells.

Dielectrophoresis

It has been shown that the DEP force acting on a particle due to an imposed electrical field, $\vec{E}(\omega)$, can be written as $$\langle \vec{F}(t) \rangle = 2\pi \epsilon_m r^3 (Re(f_{CM}(\omega)) \nabla E(rms)^2 + Im(f_{CM}(\omega))(E_{xo}^2 \nabla \phi_x + E_{yo}^2 \nabla \phi_y + E_{zo}^2 \nabla \phi_z)) \quad (1)$$

where $$f_{CM}(\varepsilon_p^*, \varepsilon_m^*, \omega) = \frac{\varepsilon_p^*(\omega) - \varepsilon_m^*(\omega)}{\varepsilon_p^*(\omega) + 2\varepsilon_m^*(\omega)}. \quad (2)$$

is the Clausius-Mossotti factor that embodies the frequency-dependent dielectric properties $\epsilon_p^*(\omega)$ and $\epsilon_m^*(\omega)$ of the particle and its suspending medium, respectively. $\omega$ is the angular frequency and E(rms) is the rms value of the applied electric field. $E_{10}$ and $\phi_i$(i=x; y; z) are the magnitudes and phases, respectively, of the field components in the principal axis directions. Equation (1), which is sufficient for the present discussion, shows there are two independent force contributions to DEP motion:

(i) A field inhomogeneity component: the left hand term depends on the real (in-phase, or capacitative) component $Re(f_{CM})$ of the induced dipole moment in the particle and the spatial nonuniformity, $\nabla E(rms)^2$, of the field magnitude. This force pushes particles towards strong or weak field regions, depending upon whether $Re(f_{CM})$ is positive or negative. This is the DEP force that allows cells to be attracted or repelled from electrode edges. It is the only DEP force component that can act when an electrode array is energized by single or dual phase signals.

(ii) A traveling field component: the right hand term depends on the imaginary (out-of-phase, or lossy) component $Im(f_{CM})$ of the induced dipole moment and the spatial nonuniformity ($\nabla \phi_x$, $\nabla \phi_y$ and $\nabla \phi_z$) of the field phase. This force pushes the particle in the same or the opposite direction to which the field is traveling depending on the sign of $Im(f_{CM})$. It allows cells to be swept along by an electric field that travels over an electrode array. At least three excitation phases must be provided for this force to arise.

These force components act independently but, by appropriate electrode array design, can be applied simultaneously to levitate cells above an electrode array while moving them over it, for example.

Cell Dielectric Properties

At low frequencies cells exhibit negative DEP (repulsion from electrode tips) but at higher frequencies, above their so-called DEP crossover frequencies, they exhibit positive DEP (attraction towards electrode tips). Different cell types have different crossover frequencies. At frequencies between about $10^4$ and $3 \times 10^4$ Hz breast cancer cells will experience positive DEP trapping while blood cells will experience negative DEP repulsion. These dielectric differences between the cancer and blood cell types can be used as a basis for cell identification, discrimination and separation. Cell sizes, cell compositions, and especially cell membrane morphologies all contribute to the dielectric differences between the cells; i.e. different cells have different dielectric phenotypes.

The inventors have found that the dielectric phenotype of every transformed cell type they have examined is significantly different from that of a more normal cell of origin, or from the same cell type following induced differentiation. This results from greater cell surface morphological complexity and a correspondingly higher membrane capacitance in the transformed cell types. Furthermore, tumor cells are normally much larger that blood cells. The effect of these combined differences is that the dielectric properties of transformed cells differ very significantly from normal blood cells. Of particular relevance to this disclosure, the inventors have measured the DEP crossover frequencies of 9 human cancers comprising 5 human breast cancer cell lines, an ascites sample taken from a patient with breast cancer, and two colon cancer cell lines. The DEP crossover frequencies of these cancer cell types suspended in solutions of 100 mS/m conductivity are shown in FIG. 1 in comparison with data for normal peripheral blood mononuclear cell types. The tumor cells all exhibit much lower crossover frequencies. These differences may be exploited for isolating populations of suspect cells from PBMNCs and lymph cell dispersions.

Prefiltering by DEP Trapping of Cells

Figure 2A:
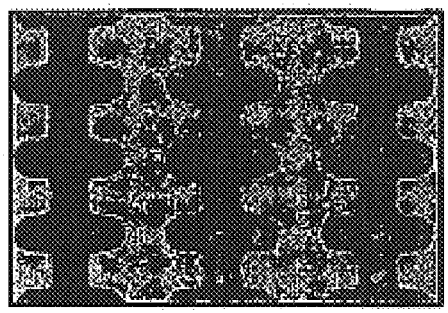
FIGS. 2A–2D are pictures showing the removal of cultured breast cancer cells from blood by cDEP affinity trapping.
Figure 2B:
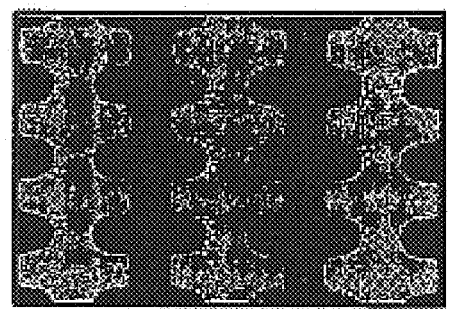
Figure 2C:
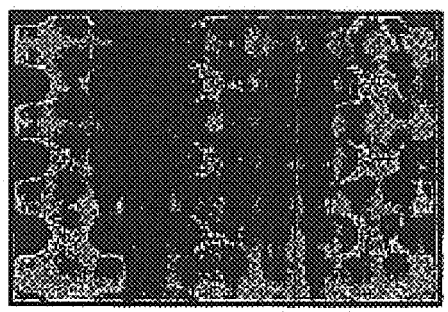
Figure 2D:
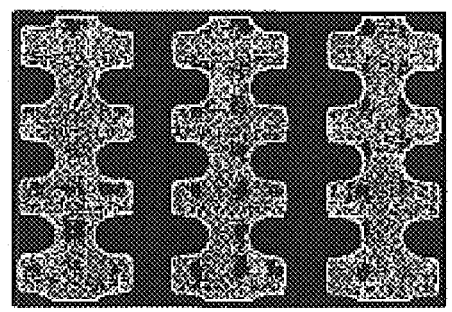

Exploitation of dielectric differences for cell separation may be accomplished in several ways. The simplest though least discriminating method is to apply a frequency that repels one cell type from one or more electrodes by negative DEP while attracting and trapping a different cell type by positive DEP. FIG. 2A shows a mixture of MDA-MB-231 human breast cancer cells and human peripheral blood. The larger breast cancer cells, about 12 $\mu$m in diameter, are readily identifiable. In FIG. 2B, a $2.5 \times 10^4$ Hz AC signal has been applied between neighboring gold electrodes (dark patterns) and fluid flow has been started from left to right. The human breast cancer cells are attracted to the electrode tips and trapped (FIGS. 2B&C). Blood cells, on the other hand, are repelled from the electrodes and carried off by the fluid. They emerge downstream, where no cell mixture was loaded, free of cancer cells, (FIG. 2D). This DEP trapping approach works well when there are large differences in the dielectric properties of target cells and other cell types in the starting mixture. For example, the inventors have demonstrated that it is possible to recover 100% of human breast tumor cells from PBMNCs even at the most dilute concentration tested in preliminary experiments, one tumor cell per $3 \times 10^5$ PBMNCs.

After flushing out the blood cells, tumor cells may be recovered by lowering the frequency below 10 kHz causing them to be repelled from the electrodes by negative DEP and released from the chamber. The inventors have found that some normal cells may be associated with the tumor cells during the trapping phase such that while recovery efficiency may be extremely good, purity may not be so good. It should be noted that at higher applied frequencies (200 kHz or more) all viable cells have been found to become trapped by positive DEP regardless of type. Therefore, DEP may be used quite generally to immobilize cells within a stream of reagents without regard to cell type if required.

In applications involving rare cancer cells, a prefilter system may be used having a surface area of about 60 cm² over which suspensions of nucleated cells can be passed at the rate of about $3.6 \times 10^6$ cells/min. This may be operated for about 6 minutes with suspensions of cells from lymph nodes and whole blood to screen $20 \times 10^6$ nucleated cells for the presence of tumor cells. Suspect cells, at a purity of >0.1%, may then be passed for high discrimination separation by the DEP-MAP-FFF in and, after subsequent isolation, for downstream molecular analysis in the integrated device (discussed in more detail in the Examples section of this disclosure).

DEP-FFF Separation

Figure 3:
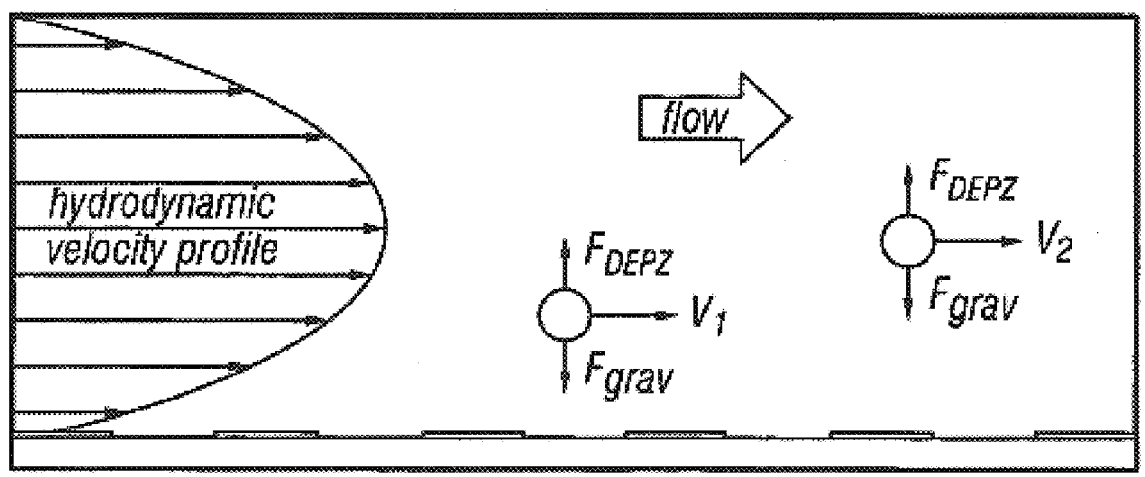
FIG. 3 is a schematic illustrating some operating principles of cDEP/FFF fractionation.

To allow high discrimination separation of tumor cells from biopsy samples or from lymph node or blood cell samples prefiltered by DEP trapping, a fractionation method termed DEP-MAP-FFF may be used. Such a method may also use immunomagnetic capabilities when needed. Instead of trapping target cells, DEP-FFF uses parallel electrodes without castellated edges to levitate cells above the electrode plain using fringing fields. The strength and inhomogeneity of the electrical field decreases with increasing height above the electrode plane and the DEP force on cells falls exponentially with height. If a frequency for which cells experience negative DEP is applied to the electrode array, cells will be levitated to a height at which the repulsive DEP force balances the sedimentation force. Cells having differences in density and/or dielectric properties will therefore be levitated to characteristic heights as illustrated in FIG. 3. This equilibrium height is given by $$h_{eq} = \frac{d}{2\pi} \ln\left\{ \frac{3\varepsilon_m U^2 A p}{2(\rho_c - \rho_m)g} Re(f_{CM}) \right\} \qquad (3)$$

for a parallel electrode geometry, where U is the electrical potential applied to the electrode array, A is a geometrical term, p is the proportion of the applied field unscreened by electrode polarization (p~1 at frequencies>50 kHz), and $(\rho_c - \rho_m)g$ is the sedimentation force.

To exploit this equilibrium levitation effect for cell fractionation, fluid flow is initiated in the channel. Fluid flows through the channel in a parabolic profile—slowest at the chamber top and bottom walls, and fastest in the middle (at about half height according to one embodiment). The velocity at height $h_{eq}$, is given by $$v_p = 6\langle v \rangle \frac{h_{eq}}{H}\left(1 - \frac{h_{eq}}{H}\right), \qquad (4)$$

where H is the chamber height and <v> is the mean fluid velocity. The fluid will then carry cells at a velocity corresponding to their levitation height. Mixed cell types starting at one end of a long chamber will therefore be separated according to their dielectric and density properties.

The family of techniques that exploits hydrodynamic flow profiles for separation is termed field-flow fractionation (FFF); hence the inventors term this method DEP-FFF. The discriminating power of DEP-FFF is extremely high in the frequency range where the cell dielectrophoretic force approaches zero (i.e. near the crossover frequencies shown in FIG. 1). Less discriminating power can be selected electrically by employing a lower frequency or by using modulated frequencies.

The inventors have made several DEP-FFF separators ranging in size from about 45 cm×2 cm to the size of a microscope slide (see section below concerning microfabrication). With the benefit of the present disclosure, those having skill in the art recognize that other sizes may be used as well. DEP-FFF separation normally take from 4 to 15 minutes to complete, but this time may vary significantly depending on the size of the device and other parameters such as sample size. For different separation times for different cell types, under different experimental parameters, see FIG. 4.

In one embodiment, a modified form of DEP-FFF may be employed in which an additional vertical force component is added that depends on immunomagnetic labeling of the cells. This may address potential concerns that some tumor cell types might not have intrinsic dielectric properties like those shown in FIG. 1 that permit their separation from normal cells by DEP-FFF alone. The inventors feel that exploitation of cell intrinsic properties, when possible, may be more desirable than requiring a labeling step; therefore, they have designed DEP-MAP-FFF separators so that exploitation of immunomagnetic labeling is an available, though non-essential, option: in the absence of immunomagnetic labeling, the device may function as a DEP-FFF separator that can discriminate cells by dielectric properties alone.

Magnetophoresis (MAP)

A particle of volume v and magnetic permeability $\mu_p$ subjected to an inhomogeneous magnetic field will experience a MAP force that is the magnetic analog of the DEP force given in equation (1)

$$\bar{F}_{MAP}=2\pi\mu_s r^3 k_{CM}(\mu_s^*,\mu_p^*,\omega_B)\bar{B}\cdot\nabla\bar{B} \quad (5)$$

Here, $\mu_s$ and $\mu_p$ are the magnetic permeability of the suspending medium and particle, respectively, R is the particle radius and, $k_{cm}(\mu_s^*,\mu_p^*,\omega_H)$ is the Magnetic Clausius-Mossotti factor describing the magnetic polarizability of the particle with respect to its suspending medium. In the static fields typically used for MAP cell sorting, $\omega_H$, the frequency of the applied magnetic field, has the value 0 and $\mu_s$ and $\mu_p$ become static magnetic permeability parameters. Furthermore, the magnetic permeability of the aqueous suspension in an immunomagnetic labeling experiment can be approximated as that of free space and the net polarizability of a labeled cell can be assumed to result from the combined effect of n identical labels that are bound to it. Finally, for a fixed geometry, the magnetic field gradient may be written as a geometry term $G_{MAP}$ times the applied magnetic field strength, $B_0$. Hence, in a biological labeling experiment we may simplify the MAP force equation to $$\bar{F}_{MAP}=n\phi\bar{G}_{MAP}B_0^2 \quad (6)$$

where $\phi$ is a constant for a given magnetic label type. This is the fundamental equation that determines magnetic capture of cells in MACS; however, the goal of the present disclosure is not to magnetically trap cells. By appropriate design of the magnetic elements that create the magnetic field and its inhomogeneity characteristics embodied in $G_{MAP}$, a MAP force may be provided that is essentially constant throughout a separation chamber and directed towards the chamber floor.

We indicated earlier that the DEP force above a parallel electrode array falls off exponentially with height h as $F_{DEP}=F_{DEP\ 0}e^{-h/h_{DEP}}$. When the electrical field conditions are chosen to provide repulsive DEP, as in DEP-FFF, the MAP force will pull an immunomagnetically labeled cell toward the electrode plane until the sum of the downward MAP and sedimentation forces are balanced by the levitating DEP force. Writing the electrical field gradient in terms of an electrode geometry term $G_{DEP}$ and the applied RMS voltage $V_0$ applied to the electrode array, the balance of forces that determines the particle equilibrium height will be given by eq. 7 below:

$$\bar{F}_{MAP}+\bar{F}_{gravity}+\bar{F}_{DEP}=n\ \phi\bar{G}_{MAP}B_0^2+[v(\rho_p-\rho_s)+nm_{label}]g+ 2\pi\varepsilon_s R^3 f_{CM}(\varepsilon_m^*,\varepsilon_p^*,\omega)G_{DEP}V_0^2 e^{-h/h_{DEP}}=0$$

where $M_{label}$ is the mass of each immunomagnetic label. If the magnetic labeling is negligible (n→0), this equation reduces to that given earlier for plain DEP-FFF. On the other hand, if magnetic labeling dominates the downward force then the decrease in h becomes approximately proportional to the logarithm of the number n of magnetic labels attached to the cell. Since in this context "dominate" means to provide a MAP force significantly in excess of the small cell sedimentation force, it will be appreciated that much smaller magnetic forces are needed in DEP-MAP-FFF than for magnetic trapping against a flow stream as used in MACS.

Note also that $V_0$ can always be chosen to ensure that no cells are pulled all the way to the chamber floor. Because, according to one embodiment, cells are separated in a FFF scheme according to their characteristic heights h in the fluid flow profile, one may separate them according to the extent of immunomagnetic labeling and, as is familiar in fluorescently-activated cell sorting (FACS), the logarithmic relationship may be very convenient for ensuring a good dynamic range when sorting different classes of cells. Therefore, when needed, MAP provides an ideal additional level of discrimination for sorting suspect tumor cell subpopulations by, for example, epithelial surface markers or receptors such as for EGF.

DEP-Mediated Cell Focusing

Cells can be manipulated simultaneously by DEP, which attracts or repels them from electrode edges, and twDEP, which transports them parallel to the plane of the electrodes. A spiral electrode configuration may be used to exploit these effects simultaneously for concentrating cells and achieving electrically stimulated cell lysis. The spiral array in one embodiment includes four parallel electrode elements that are energized by signals of the same frequency but phases of 0°, 90°, 180°, and 270° to create a concentric traveling field that sweeps towards the center of the spiral. Excitation by phases 0°, 270°, 180°, and 90° results in a field that sweeps outward towards the periphery of the spiral. Signals of 0°, 180°, 0°, and 180° phases produce a stationary field pattern that can be used for DEP trapping, levitation, or, at very high field strengths, cell bursting.

Figure 5:
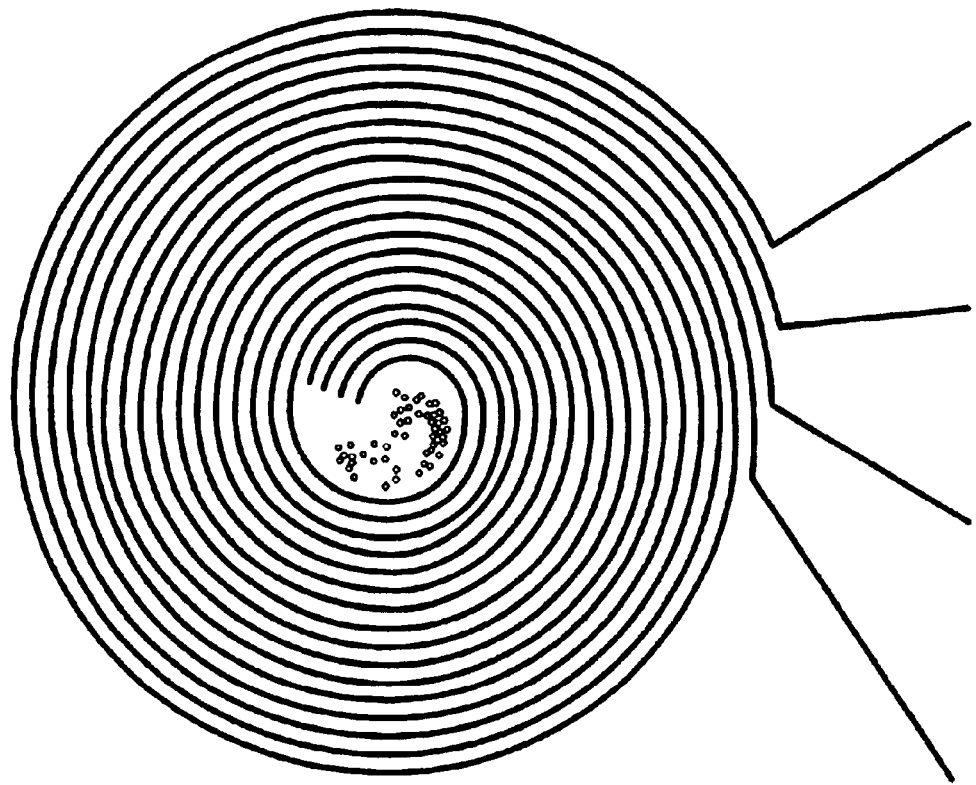
FIG. 5 is a picture showing a spiral electrode array that may be used to focus cells by twDEP.

An example of cell trapping and focusing is shown in FIG. 5 where HL-60 human promyelytic leukemia cells have been focused from a scattered state to the center of a spiral in about 15 seconds. In one embodiment, the spiral arms of the electrode array may be extended until they almost touch at the center of the spiral allowing greatly increased cell concentrations to be achieved. The inventors have applied this technique to trap and focus murine erythroleukemia and human breast cancer cell lines from a flow stream, and separate breast and leukemia cells from blood cells. Also the inventors have successfully separated erythrocytes parasitized by the malarial agent *Plasmodium falciparum* from their uninfected counterparts with this technique.

In one embodiment, five spiral array segments may be used to trap cell subpopulations as they emerge at different times from a DEP-MAP-FFF separator stage of an integrated device. By injecting assay beads into the stream of cells as they emerge from the separator and before they are trapped, and by then applying a swept field to the spiral electrodes, cells and beads may be focused to the center concurrently to form a highly concentrated mixture.

Electro-Mediated Lysis of Cells

Once a target cell population has been successfully isolated, subsequent molecular analyses normally require that the cells be disrupted to release intracellular proteins, RNA, and DNA. Approaches to this include exposure to detergents or other lysing reagents. Although these methods can be used in systems and devices disclosed herein, cells may be lysed electrically using large AC electrical fields. DEP manipulations typically involve local electrical fields less than $10^4$ V/m and the inventors have shown that cells can sustain prolonged (40 minutes and longer) exposure to such fields without loss of viability or activity. Depending on the electrode geometry, voltages of the order of 1 V RMS are used to achieve this.

Figure 6A:
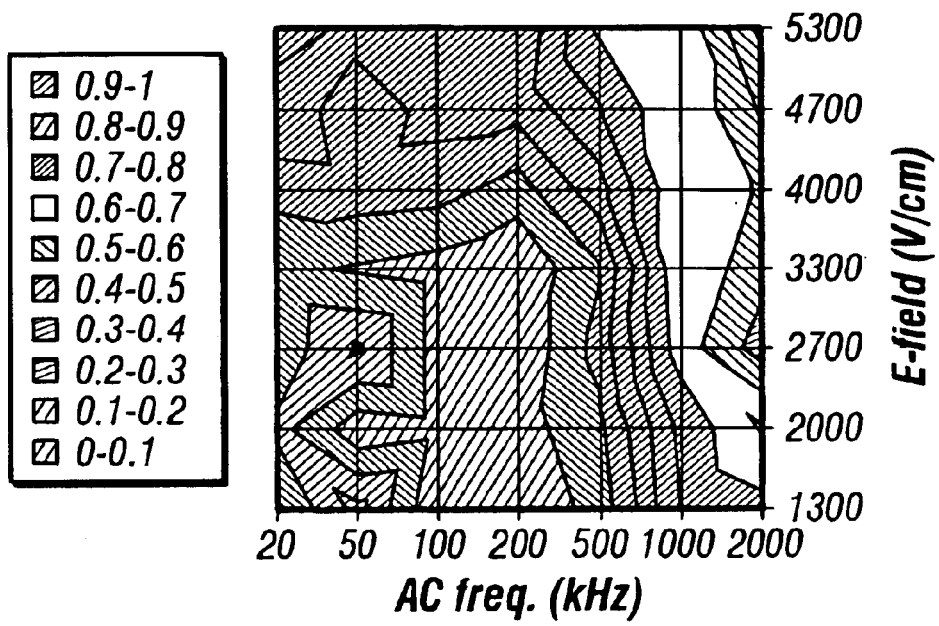
FIGS. 6A–6B are charts showing field/frequency bursting characteristics of (A) T-lymphocytes, and (B) MDA-MB-435 breast cancer cells.
Figure 6B:
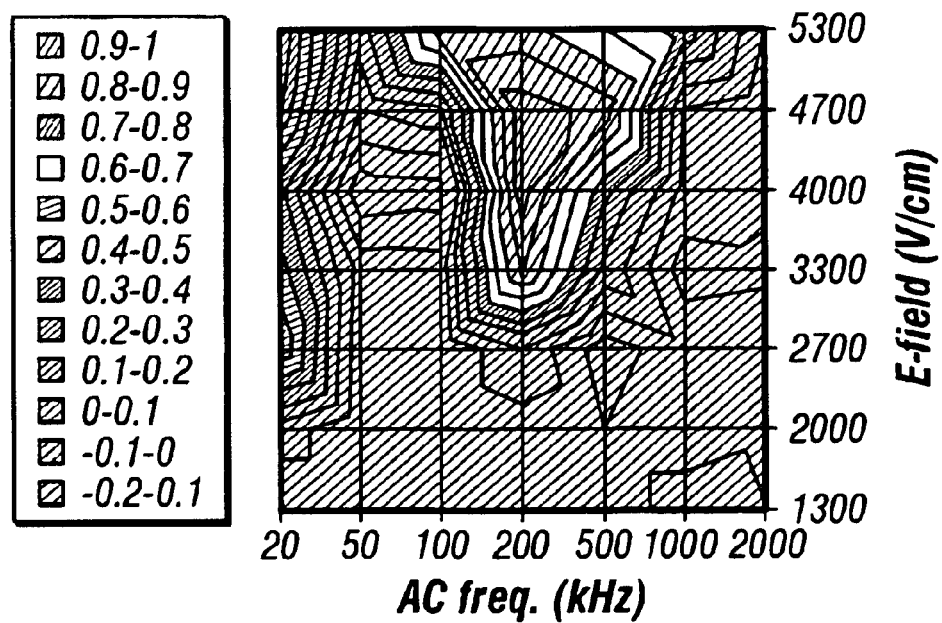

However, higher AC voltages may be applied to create fields that can burst cells. Depending on the cell type, at about $5 \times 10^4$ V/m, temporary membrane electropermeabilization occurs, and this can be used to load reagents into cells. Above about $2 \times 10^5$ V/m, instantaneous destruction of the cell membranes occurs. The inventors have found that different cell types have characteristically different susceptibilities to destruction. FIG. 6A illustrates the field intensity vs. frequency dependency for the disruption of human T-lymphocytes and FIG. 6B shows results for human MDA-MB-435 breast cancer cells. Clearly the cells burst in characteristic, and distinct, frequency and field ranges. A useful feature is the ability to select electrically whether to reversibly permeabilize or totally disrupt all, or select subpopulations, of cells that have been trapped on an isolation electrode.

In one embodiment, electro-mediated cell lysis may be utilized at the center of the spiral isolation segments to release molecular species from target cells into the immediate vicinity of the assay beads mixed and concentrated with them.

Microfabrication

Electrode arrays for use in, for instance, a separation according to embodiments of the present disclosure may be made by microlithography as is known in the art. The inventors have built DEP chambers and separators over a wide range of sizes from about 200 $\mu$m-45 cm with capacities of 10 $\mu$L to 4 mL. The use of silicon and glass and micromachining methods may be used for cases where integrated electronics and sensor capabilities are required that other fabrication methods cannot provide. In other cases, a combination of flat glass and injection-molded polymers may be used to fabricate the devices disclosed herein by methods known in the art. Small devices may be made by silicon and glass micromachining, and can be reproduced by single layer lithography on a flat glass substrate (for the electrodes) with all fluidic channels molded into a clear polydimethylsiloxane (PDMS) top. Molding PDMS has been suggested as a much more cost effective approach than micromachining glass and silicon; it comes as a clear liquid that can be cast or injected into a mold. Devices of the present disclosure may be designed to handle not only small (about 20 $\mu$L) samples but also larger volumes (~10 mL or more). To accomplish this, a microfluidic front-end is clearly unsuitable because it would be unable to process large samples at reasonable rates. In one embodiment, the sample may be enriched as it passes through the device and to simultaneously reduce its volume. In this way a microfluidic stage, with its advantages of small sample requirements and rapid processing capabilities, may be seamlessly interfaced to the macroscopic world to complete the molecular analysis.

Magnetic Field Generation

Figure 7:
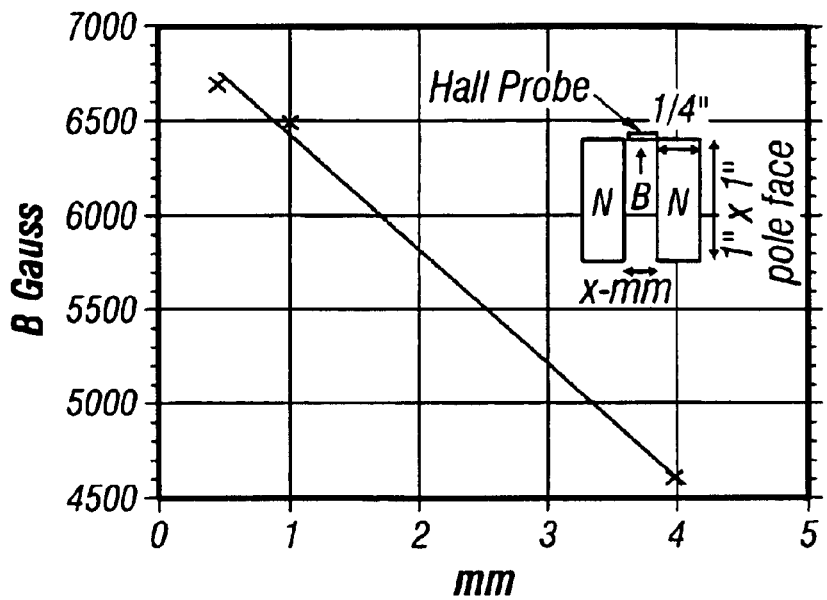
FIG. 7 is a graph showing magnetic field strength emerging from two opposing magnets.

The MAP force to be used in conjunction with DEP-FFF requires a magnet having rather unusual properties, namely the product of the magnetic field strength and its inhomogeneity need to be effectively constant over the entire length of the separator. To achieve this, one may use several flat magnets of SnCo or NdFeB materials placed a parallel configuration in an opposing pole orientation. FIG. 7 shows two magnets in this configuration. The field lines experience compression in the space between the opposing poles and emerge in a relatively homogeneous distribution. Controlled inhomogeneity in the field may be created by using a composite material made of sintered iron spheres in the field path.

The field strength and homogeneity (in the absence of the sintered iron elements) has been tested for two 6 mm thick SnCo magnets having 25 mm×25 mm pole faces and a "free field" of 0.22 T in air. The field of the opposing pole configuration was measured with a directional Hall probe. Field strengths in excess of 0.4 T were measured (FIG. 7) for pole spacings of 4 mm or less and the horizontal field component was below 5%. Based upon the inventors' measurements of the magnetic fields used in small MACS separators, these intensities are more than sufficient to achieve magnetic positioning of immunomagnetically-labeled cells in DEP-MAP-FFF.

The following examples are included not for limitation but, rather, to demonstrate specific embodiments of the invention. It should be appreciated by those of skill in the art that the techniques disclosed in the examples which follow represent techniques discovered by the inventors to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Design Issues

Figure 8:
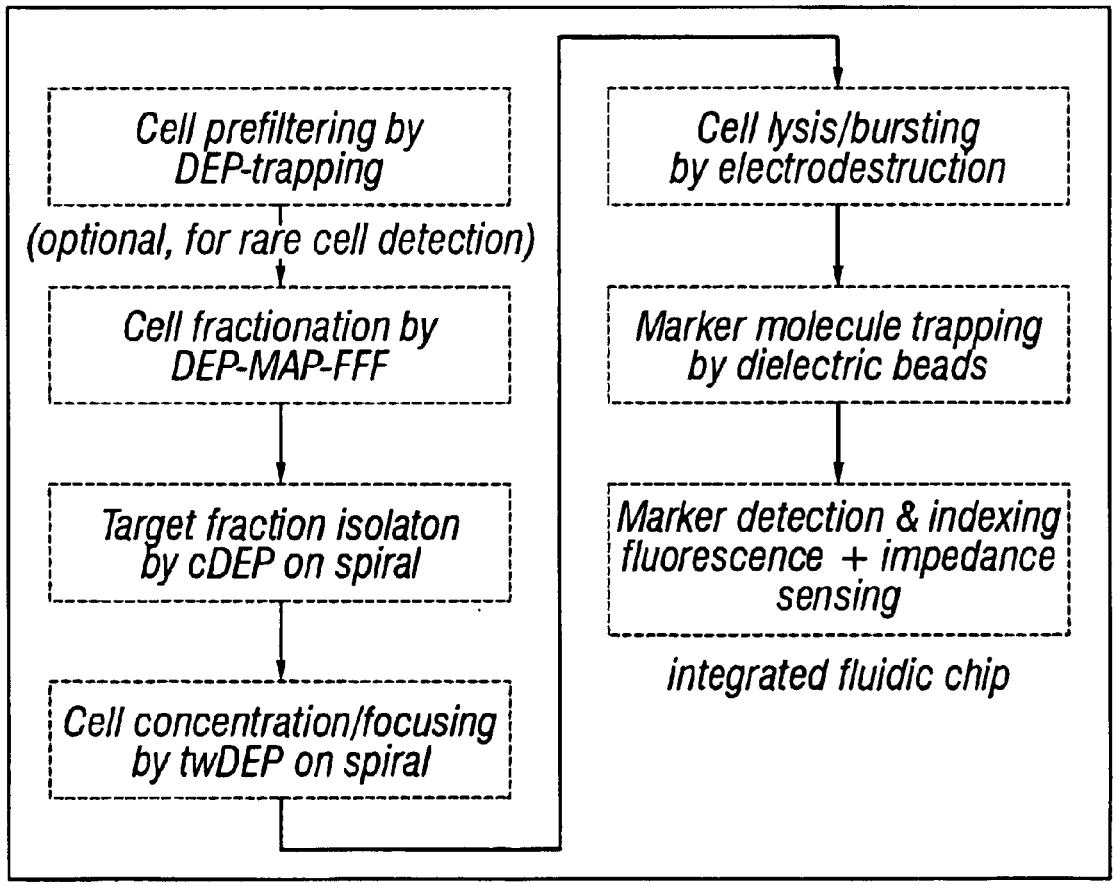
FIG. 8 is a flow chart illustrating functional stages of a device for cell isolation and analysis.

In one embodiment, the present disclosure is directed to an integrated fluidic device able to sort, isolate and burst target cells from clinically relevant samples and to execute molecular marker assays on them rapidly and automatically. FIG. 8 shows a functional block diagram of a complete integrated device and FIG. 9 shows a design for the system.

Prefilter

Figure 9:
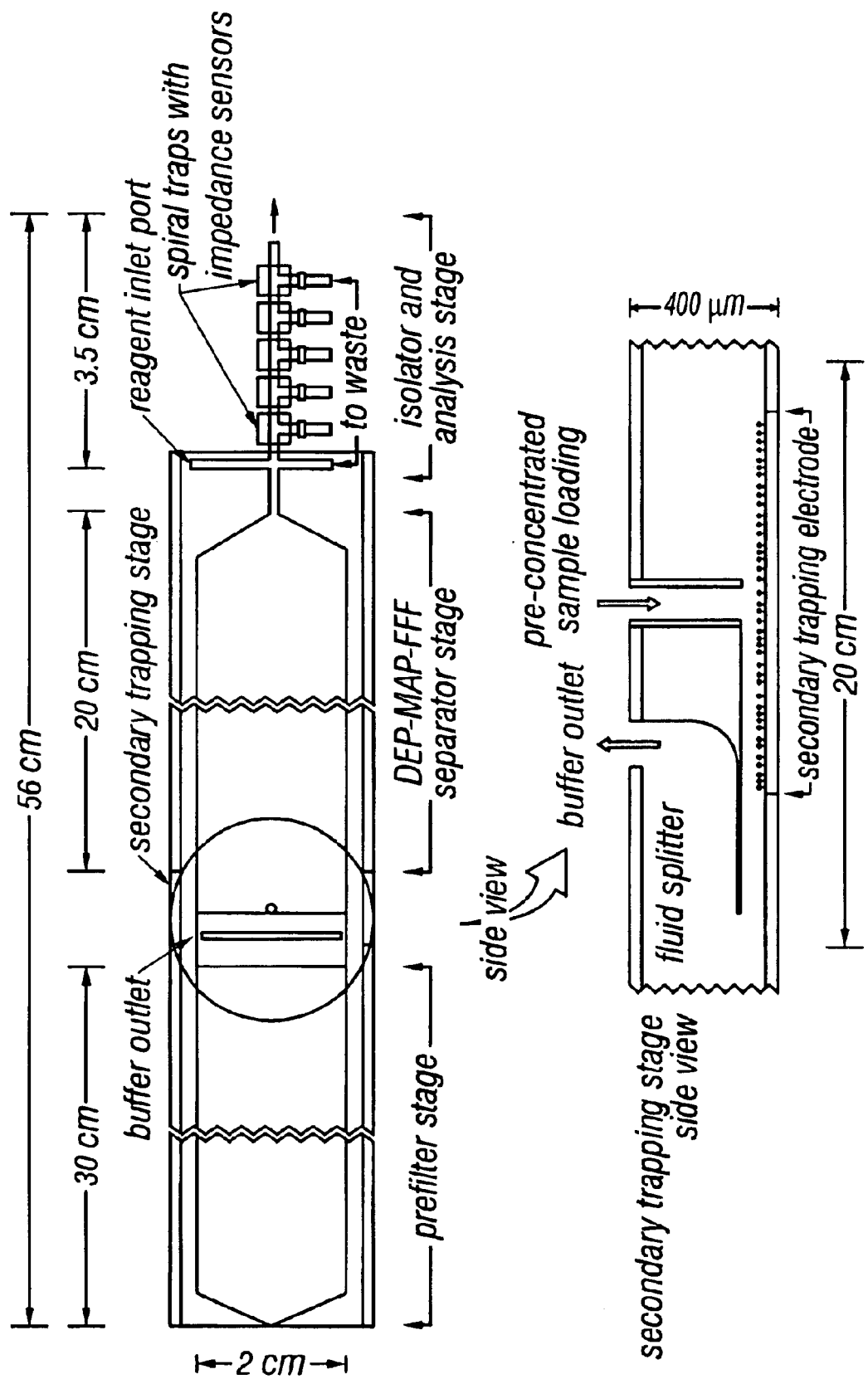
FIG. 9 is a schematic of an integrated fluidic system, including a prefilter stage, a separator stage, and an isolator and analysis stage.

FIG. 9 shows the design of the prefilter and DEP-MAP-FFF cell fractionation stages of the device. The prefilter is essentially a scaled-up version of a DEP cell trapping device. Its purpose is to cope with the huge numbers of cells that need to be sorted in rare cell detection applications. It is aimed at capturing all cancer suspect cells even at the expense of retaining some normal cells. The scaled-up prefilter is designed, in one embodiment, to process a sample of $\leq 10$ ml volume containing $\leq 2 \times 10^7$ cells in $\leq 10$ minutes at a maximum rate of $3.6 \times 10^6$ cells per minute. It is designed to extract from that sample suspect cells that will be passed to the second, high discrimination cell fractionation stage (discussed below).

Samples may be exemplified by peripheral blood from which erythrocytes have been lysed, dispersions of lymph node tissue, or dispersed biopsy cells. To achieve sorting in $\leq 10$ minutes, the prefilter may sort $\leq 1000$ $\mu$L of cell suspension per minute. This may be accomplished by a DEP trapping array lining the floor of a chamber 20 mm wide, 400 $\mu$m high and 30 cm long. These dimensions ensure that (1) suspect cancer cells in the mixture are guaranteed sufficient time when traversing the chamber to sediment close enough to the DEP electrode array to be trapped by an applied 50 kHz field while normal blood cells are repelled; (2) hydrodynamic forces experienced by trapped cells remain sufficiently weak not to dislodge them from the electrode array; and, (3) cell density remains sufficiently low that suspect cells are not knocked away from electrodes by collisions with an over-abundance of other cells.

After processing the starting suspension, clean eluate may be passed through the prefilter at about 400 $\mu$L/min to wash away remaining untrapped cells. During this rinsing phase, the DEP prefilter trapping electrode may be de-energized while the secondary trapping stage remains energized. Suspect cells in the prefilter stage may be released and carried to the secondary trap. This consolidation of trapped cells is made possible by the removal of the large concentration of normal cells from the system. Throughout these early phases, emerging eluate may be sent to waste.

After the consolidation step, the secondary trapping stage may contain the suspect cancer cells together with some entrapped blood cells. Based on the inventors' experience, this stage is expected to collect a total of no more than $2 \times 10^5$ "suspect" cells at this stage. The suspect cells may include a limited number of monocytes, some macrophages, and any other large circulating cells including all of the true cancer cells. This number of cells is ideal for high discrimination sorting by DEP-MAP-FFF because the cell density has been sufficiently reduced for cell—cell interactions to be ignored. A major advantage of the prefilter design is its relative tolerance of such cell—cell interactions.

Magnetic Antibody Labeling

The cells in the secondary trapping stage may be incubated with magnetically labeled antibodies if MAP separation is to be utilized in the next step of cell isolation. Also, fluorescent antibodies, appropriate for surface marker detection much further downstream in the device, may be added at this point. To accomplish labeling, antibodies may be injected into the port provided for this purpose while the cells are held in place on the electrode by DEP forces from a field of, in embodiment, about 250 kHz. Once fluid flow has stopped, a DEP field of about 3 V peak—peak may be alternated between about 10 kHz and about 250 kHz at about 10 second intervals to alternately levitate and trap the cells, gently stirring them with the antibodies. Following incubation, the DEP field may be switched to about 250 kHz to trap the cells while the antibodies are washed away and the cells are rinsed with fresh buffer.

DEP-MAP-FFF Injection

Following the optional antibody-labeling steps, a 0.5 V, 10 kHz signal may be applied to release the suspect cells from the secondary trapping electrode without levitating them. Fluid flow may be initiated in the prefilter stage and the cells may be flushed into the DEP-MAP-FFF stage via the fluid splitter. Because of the dimensions of the chambers and the splitter position, the suspect cells may be carried into the DEP-MAP-FFF stage in 20 $\mu$L of eluate. A syringe pump at the end of the DEP-MAP-FFF stage may be used to control the sample flow.

In applications such as analysis of fine needle aspiration biopsy samples, the starting cell count may be about $2 \times 10^5$ cells or less, and the prefiltering step becomes superfluous because the DEP-MAP-FFF fractionator can handle such small samples without undesirable cell—cell interactions. Such samples may be injected into the preconcentrated sample loading port at the concentrator injection stage for the optional antibody labeling steps and thence directly into the DEP-MAP-FFF sorter.

DEP-MAP-FFF Fractionation

During and after injection of the cell sample from the prefilter stage, the DEP electrode array in the DEP-MAP-FFF separator stage may be energized with a frequency appropriate for separation, typically in the 20–80 kHz range. With flow stopped, cells may be allowed sufficient time to reach equilibrium heights at which the magnetic, DEP and gravitational force fields acting on them are balanced. Based on DEP-FFF experiments this so-called relaxation time need not exceed five minutes. Following relaxation, fluid flow through the DEP-MAP-FFF stage may be initiated and cells may be carried through the chamber at characteristic velocities in accordance with their positions in the parabolic flow profile controlled by the balance of DEP, MAP and gravitational forces. Based on DEP-FFF experiments, this separation step should take, in one embodiment, 12 minutes or less.

Trapping of Cell Fractions

As at the interface of the prefilter and DEP-MAP-FFF stages, a split flow may be used between the DEP-MAP-FFF stage and the isolator and analysis stage so that only flow close to the bottom of the separator, in which cells may emerge, is passed through. The remaining eluate may be extracted from above and sent to waste. A controlled flow of analysis beads may be injected into the flow stream as it emerges from the DEP-MAP-FFF separator and enters the isolation and analysis stage. This may mix analysis beads with the emerging cell fractions.

The cell isolation stage may be divided into 5 separate electrode array segments, each capable of trapping and concentrating a separate fraction of cells that emerges from the separator. Before any cells have emerged, a non-traveling 10 kHz field may energize the first 4 segments of the isolation stage. This may levitate both cells and beads by negative DEP and prevent them from settling on those segments. However, the fifth segment may energized at 500 kHz, a frequency at which all cell types and the beads may become trapped. Therefore, the first cells to emerge, and the beads mixed with them, may be carried across the first 4 segments and be trapped on the fifth by positive DEP. After an appropriate time span to isolate the first fraction of cells on the fifth segment, the 4th segment of the trap may be energized at 500 kHz so that cells emerging subsequently may be trapped there together with the beads that were mixed with them. At appropriate time intervals, the 3rd, then the 2nd, and finally the $1^{st}$ trap may be similarly energized at 500 kHz. After completion of this process 5 different cell fractions may have been isolated and trapped, each containing cells that emerged from MAG-DEP-FFF separation between different time limits together with beads that were mixed with them. Although here described with respect to five segments, those having skill in the art recognize that any number of segments may be used.

Based on the inventors' knowledge of DEP-FFF and predictions about MAG-DEP-FFF, cells combining the smallest sizes, most uncomplicated surface morphologies and lowest concentrations of magnetically-labeled surface markers may emerge early and be trapped in segment 5. Conversely, cells combining large size, complex surface morphology and high concentrations of surface markers may emerge last and be trapped in segment 1.

Histological Analysis of Cell Isolates

Optionally, the cells trapped in the different segments of the isolation and analysis stage may be treated with antibodies or stains by injecting these through the reagent port provided for this purpose. So long as the histological reagents do not affect cell viability, the cells may be held in place by positive DEP during perfusion and treatment. Several staining steps can be used and excess reagents or antibodies washed away, as needed. Glass and/or clear PDMS may be used for constructing the separation chambers. Therefore, after staining, cells isolated in the five segments may be compared and contrasted in situ by optical and/or fluorescence microscopy by a pathologist. If desired, additional reagents for the next step of cell analysis may be added at this point.

Focusing/Concentration

Having trapped cells and beads on the five segments of the isolator stage, optionally examined them with histological stains, and perfused them with the reagents needed for the next step in analysis, the cells may be focused to form a dense mixture with the beads. To accomplish this, the spiral electrodes in all five segments of the isolation stage may be energized with a four-phase field swept in frequency from 10 kHz to 200 kHz to provide a twDEP force directed towards the center of each of the five spirals. Because of the established dielectric properties of mammalian cells and the customized dielectric properties of the beads, this may sweep cells and beads of all types towards the center of the spiral on which they were originally trapped. It is believed that this process should take no more than 1 minute and should result in a dense conglomeration of cells and beads at the center of each spiral. In this way, each isolated fraction may be concentrated to a density of ~$10^9$ cells/ml together with ~$10^{10}$ beads/ml suspended in the reagent mixture that was perfused prior to focussing.

Cell Bursting

Once the cells and beads are concentrated, electromediated lysis of the cells can occur. This may be achieved by applying a strong AC voltage to the spiral electrode (e.g. 15 V peak to peak). Those having skill in the art recognize, however, that any other voltage suitable to cause bursting may be used.

Molecular Analysis

The liberation of intracellular components following cell lysis may allow their reaction with the perfused reagents and their interaction with the surfaces of beads (if present). Based on experiments reported in the literature for the hybridization of rare mRNA's in concentrated cell lysates with probes carried on beads, these reactions occur very rapidly, typically within a few minutes.

Detection

After an incubation time of 15 minutes, the target mRNA's should have hybridized with complimentary probes on beads. The spiral electrode segments may be energized with a 500 kHz non-travelling field to trap the beads at this point. Cell debris is not attracted by positive DEP and may be washed away from the beads. Indeed, relatively harsh reagents can be added to clean up the beads at this point providing those do not degrade the mRNA's bound to different bead types or damage the beads. After washing the beads free of debris and unhybridized molecules, the beads may be perfused with secondary fluorescent probes for target mRNA sequences. In this way, target sequences on the bead surfaces may be fluorescently labeled. Following additional washing steps to remove unbound secondary labels, the spiral electrodes may be energized with a 10 kHz signal to release the beads. At this point, eluate flow may be commenced through one spiral segment after another and the beads may be examined as they pass through the proximal impedance sensors.

Simultaneous fluorescence analysis may be used to quantify the amount of mRNA secondary label bound to each bead, and the AC impedance characteristics may be used to identify each bead/probe combination (and hence index the mixed assays). This process should take about 15 minutes.

Total Analysis Time

If all steps shown above were to be undertaken, the entire analysis from start to finish may take about 2 hours. This would include prefiltering cells from a starting mixture with a detection limit that should approach 1 cancer cell per $10^6$ normal cells; isolating tumor cells based on their dielectric properties and, optionally, surface immunomagnetic markers; histological analysis of the cells in comparison with other isolates; and molecular analysis for up to 10 different mRNA's.

Alternatively, if immunomagnetic markers and histology steps were omitted, the cell sorting, isolation, and molecular analysis would take about 45 minutes from start to finish.

EXAMPLE 2

Fabrication Issues

Fabrication of Electrodes

Electrode arrays may be fabricated using standard microphotolithographic techniques. Briefly, one may start with a clean glass substrate coated with 70 Å titanium and 1000 Å gold. Coating to NNN-S-450 specification may be done either commercially by Thin Film Technology, Inc., and guaranteed to be of uniform deposition, pinhole-free quality and able to withstand 10,000 psi lifting force, or using sputtering. The resulting gold blanks (up to 125 mm×125 mm in size) may be spin coated with Shipley photoresist which is exposed to UV light through a mask using a mask aligner (AB Manufacturing, San Jose). The resulting pattern is developed and inspected and the gold and titanium layers are then etched in two steps with $KI/I_2$ and hot HCl, respectively. Masks are designed by an IC CAD layout package (Design Workshop). Masks are either made commercially by the e-beam method (masks up to 6"×6" and features down to <1 µm) or else produced by photographically reducing a 10×version of the mask printed on, for instance, a Hewlett-Packard DesignJet 2500CP printer at 600 dpi (final mask size up to 4.8"×4.8" and features down to 4 µm).

To prevent cell sticking, electrodes may be silanized to produce a hydrophobic coating or else coated with TEFLON. Silanization is routinely accomplished with SigmaCote. TEFLON coating is accomplished by solvent deposition from a fluorocarbon carrier and subsequent baking onto silanized electrodes or by sputtering (in collaboration with the Stanford Microfabrication Laboratory).

Device Structural Fabrication

The glass substrate of the electrode array constitutes the lower wall of the device. Two approaches may be taken to construct device tops. In the first, the top wall consists of 4 mm glass into which holes are drilled for inlet and outlet port connections using a triple-tipped diamond drill. PEEK or TEFLON tubes are glued into the holes and cut off flush on what may become the inside surface of the device to form fluid interconnects. The two facing walls of the device are either sealed along their long edges with UV-curing epoxy glue, held in place by multiple small plastic clamps, or clamped by a single metal frame machined for the purpose. Fluid flow paths inside the device are defined in this construction method by a gasket of between 50 and 400 µm thickness, as required, having a slot cut wherever fluid flow is desired. The inventors have successfully used gaskets of PTFE, Gore-Tex, RTV and PDMS polymers. This method is adequate for simple flow paths but for the more complex flow paths in the integrated microfluidic component required for the multiple-segment spiral isolation and impedance sensing stage, a method using injection molded seals may be used. Seals may be made for this purpose in a separate mold and then sandwiched between a plain top and bottom as described above or the top of the device may be machined from Lucite and have seals injection molded directly into it. In this case the seals are made to extend above the surface of the top plate by a distance equal to the desired channel thickness. Simply pressing the device top plate against the device bottom then forms the required flow path and this allows for easy disassembly and cleaning without damaging a gasket. The molding material used to form the seals is PDMS, a resilient polymer that is durable, biologically inert, sufficiently compressible to form a good seal against fluids even with limited compression force, and transparent. In order to realize complex seal patterns, the inventors use a small Sherline CNC milling machine that operates directly from a CAD layout. In this way, flow paths that are mathematically defined can be cut directly into device top blanks under computer control. This allows well-defined, smooth fluidic pathways to be fabricated quickly and reproduced easily.

Fluid Flow Control

Fluid flow may be controlled by digital syringe pumps (KD scientific, Boston, Mass.) each capable of holding two syringes of different barrel sizes. The inventors have found that the useful flow rate from these pumps (i.e. for which there is an effective absence of pulsations due to stepper motor action) extends over 7 decades from 0.01 $\mu$l/min to 70.57 ml/min. For the fully integrated system as many as four pumps may be needed to allow automated sample control in the DEP prefilter, DEP-MAP-FFF stage and isolator. The pumps can be daisy-chained for convenient serial control by computer or manually controlled. Flow valves may be needed to control some waste and outlet lines. These can all be mounted off the fluidic device. Low dead volume valves from Lee may be used for these fluid control needs.

Conductivity Measurements

Conductivity measurements of suspending medium solutions may be made with a Cole-Parmer 19101-00 electronic conductivity meter using either a flow-through or dip electrode cell with platinum black coated platinum electrodes.

Microscopy

Devices under test may be mounted on the stage of a Zeiss Axiovert S-100 inverted microscope (magnification X5–X600) equipped with video recording and image analysis capabilities. This allows direct observation of any section of the transparent-walled devices and permits manual or automated visualization of cells. The microscope is equipped with epifluorescence and a sensitive three color CCD camera that is used for fluorescence microscopy. By quantifying the signal with software, fluorescence of molecular probes may be accomplished. For detection of molecular probe fluorescence signals, the inventors have an Oriel MS257 high sensitivity fiber optic tuneable dye laser spectrometer system and a Zeis Axiovert 405M inverted microscope equipped with a Photometrics CH210 liquid nitrogen cooled photon-counting camera.

Electrical Signals

Electrical fields for DEP/FFF and DEP trapping may be provided from 2 Hewlett-Packard 33120 signal generators (up to 15 V peak—peak, frequencies up to 50 MHz) with FM and AM sweeping capabilities. For twDEP focusing on the spiral electrode, four sine signals in quadrature are required and a digitally synthesized source based on a quadrature-phase numerically controlled oscillator chip may be used. This may be interfaced to a computer to provide quadrature signals up to 12 MHz and up to 12 V peak—peak with modulation characteristics that can be software controlled. Signals may be monitored with a Tektronix 200 MHz digital oscilloscope.

Magnetic Fields

Figure 11:
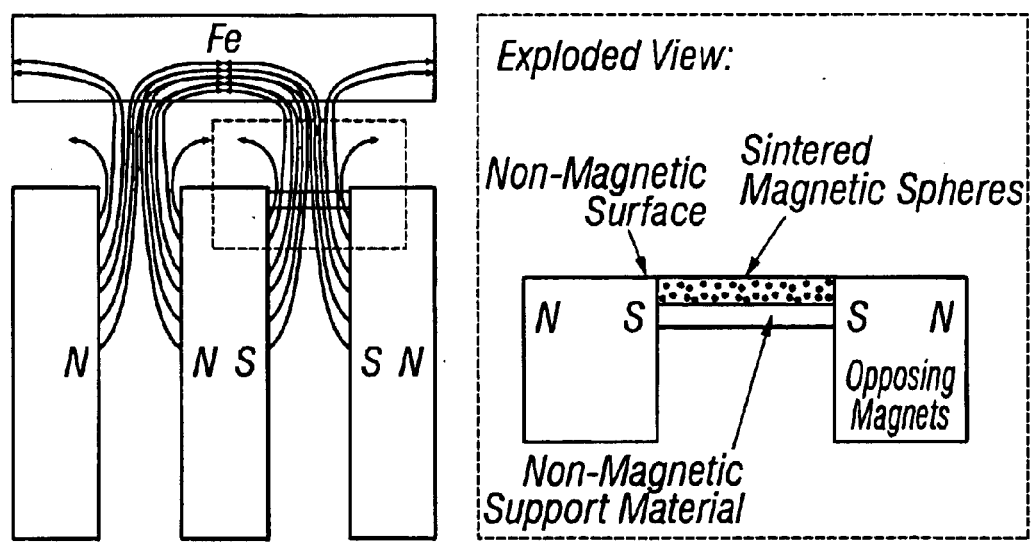
FIG. 11 is an end view of a magnetophoresis assembly. The magnets are SmCo or NdFeB. The separation chamber sits in the magnetic flux gradient just above the sintered iron spheres. Sintered iron spheres may be replaced by iron wedges or filaments to produce different desired flux gradient characteristics.
Figure 10:
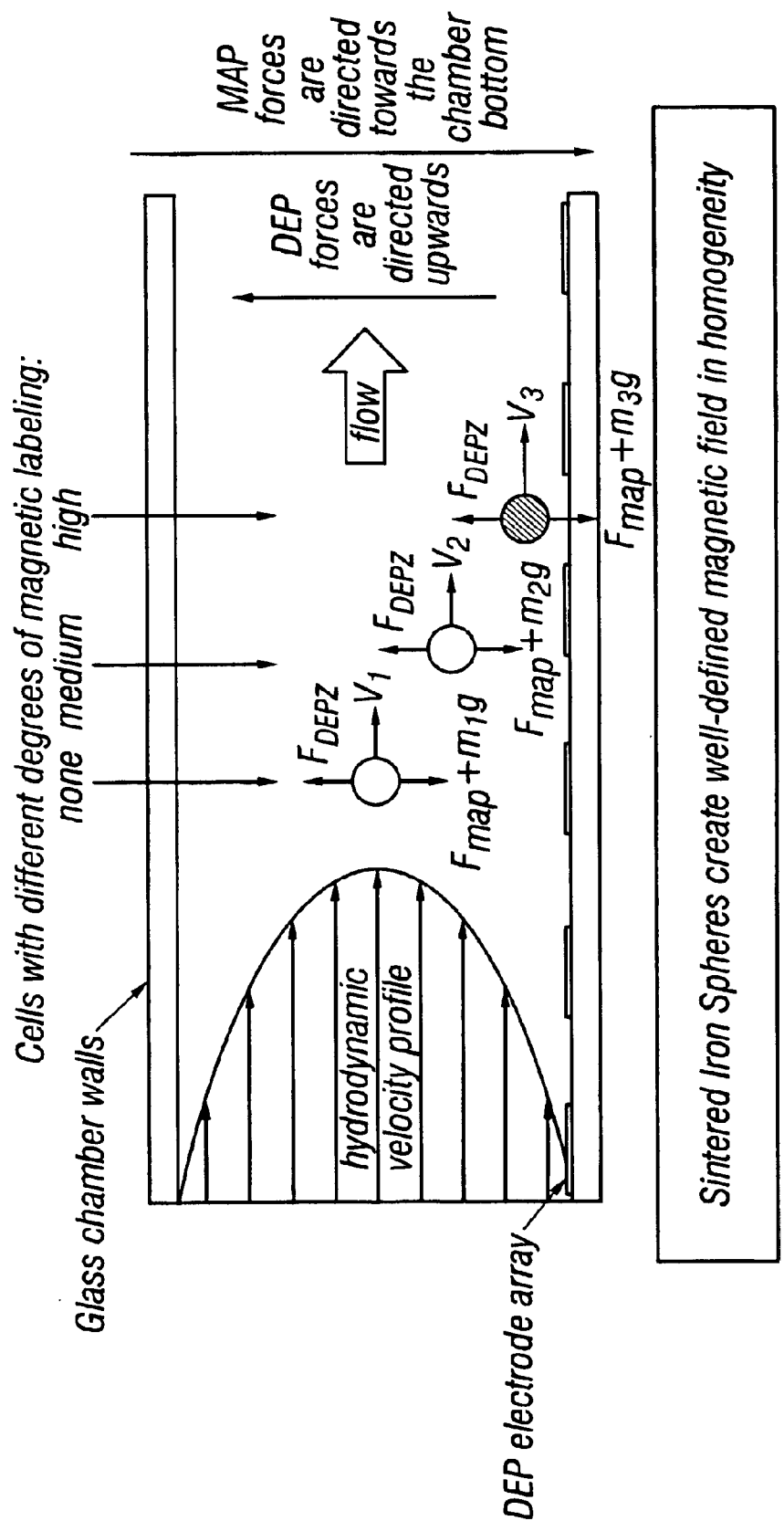
FIG. 10 is a schematic showing a short section of a DEP-MAP-FFF chamber.

An important task in developing the DEP-MAP-FFF method is designing magnetic components to provide field distributions that achieve an appropriate distribution of $\overline{B}\overline{\nabla}.\overline{B}$ throughout the separation chamber. The design for the magnet system is shown in FIGS. 10 and 11. This arrangement of magnetic pole pieces may allow the field to be produced over the large area needed for a full sized DEP-MAP-FFF separator. Parallel SmCo or NdFB permanent magnets (e.g., 0.5 Tesla) may be used to provide fields closer to 1 Tesla. The field enhancement may be accomplished by exploiting boundary conditions on $\overline{B}$ and $\overline{H}$ at the iron surface. The enhancement is controlled by the shape of the Fe component and, in particular, by the size of the effective pole face. Field inhomogeneity may be controlled by the sintered iron particles underneath the DEP-MAP-FFF separation channel. In fact, principles used for creating MAP forces in the DEP-MAP-FFF separator are the same as used in existing MACS separators. However, the iron field enhancer and shapers may rely upon a well-defined microgeometry rather than the random geometries used in present day MACS separators. It should be borne in mind that the MAP forces needed to control the height of cells in a flow stream are about an order of magnitude less than those needed to trap cells in a column against hydrodynamic forces. For this reason the inventors believe that SmCo or NdFB magnets may be adequate.

Magnetic simulations may be undertaken while magnets are being built and tested using directional Hall probes to ascertain the field strengths and spatial inhomogeneity properties. In this way, design, simulation, construction, testing and refinement steps may go hand-in-hand to produce magnets suitable for the MAP requirements of this project.

Computer Simulations

The distribution of the electrical and magnetic fields within the fluid between the chamber walls determines the DEP and MAP forces experienced by cells. Although the inventors' early electric field calculations were performed by the charge density method, implemented by FORTRAN, more recently the inventors have used the ANSYS multiphysics finite element analysis package to compute field distributions and have used the post-processing capabilities of MATLAB to derive the corresponding DEP force distributions.

DEP electrode geometries known in the art may be used. To achieve optimal $\overline{B}\overline{\nabla}.\overline{B}$ distributions for DEP-MAP force balance, however, one may need to use the ANSYS package to do simulations as a function of the size, shape and placement of the magnets, the iron field concentrator, and the sintered iron components. The ANSYS package allows simultaneous electrical and magnetic computations so that it is ideal for modeling the behavior of the DEP-MAP force balance properties of various geometries.

Finally, the ANSYS package also allows modeling of hydrodynamic characteristics of flow channels and the inventors plan to model the behavior of the fluid and cells as they pass though the integrated device, particularly in the fluid inlet and egress regions. This may be important in the interface regions between stages of the system to ensure the design allows efficient sample transport without "dead" spaces in which cells may settle.

DEP Trapping

Where needed, a 500 kHz field at 5 V p—p may be used to trap cells by DEP. This frequency is sufficiently high to penetrate the cell membranes efficiently without causing damage and induces a strong DEP body force on the cells, trapping them efficiently against fluid flow. DEP trapping may be used in four ways within the integrated system: (1) for cells being concentrated in the second segment of the prefilter following elution of normal cells and for small samples injected directly before the DEP-MAP-FFF stage; (2) for cell subpopulations that are isolated in the spiral electrode segments after elution from the DEP-MAP-FFF stage; and, (3) for holding cells in place during reagent perfusion at several steps in processing; (4) for holding beads in place for reagent perfusion following cell lysis and hybridization steps.

DEP-MAP-FFF Separation

Based on the inventors' experience with DEP-FFF, up to $2 \times 10^5$ cells can be analyzed without cell concentration becoming so large as to cause perturbing cell—cell interactions in the size of DEP-MAP-FFF fractionator chosen here. For samples expected to have a high concentration of suspect cells, such as dispersed cells from biopsies of suspected tumors or fine needle aspiration biopsies, $2 \times 10^5$ cells are sufficient to ensure that tumor cells, if present, may be sufficient for molecular analysis. In such cases, up to 20 $\mu$L of cell suspension may be injected via the preconcentrated sample loading port. For samples in which the concentration of suspect cells is expected to be so low that there is unlikely to be sufficient suspect cells in a $2 \times 10^5$ cell sample, prefiltering may be necessary. Samples such as peripheral blood mononuclear cells or dispersed lymph node cell populations fall into this category.

Following injection of a 20 $\mu$L sample or prefiltering, as appropriate, the secondary trapping electrode may be energized at 250 kHz frequency and 5 V p—p. All cell types may be trapped from the flow stream by DEP on the electrode in the entrance region of the DEP-MAP-FFF separator stage. Sample injection into the DEP-MAP-FFF stage may now occur with an appropriate DEP levitation signal applied. After cells have been given time to reach equilibrium heights (2–5 minutes) under the influence of DEP, MAP and gravitational forces, carrier medium flow may be started from a digital syringe pump (KD scientific, Boston, Mass.). The first cell subpopulations should begin emerging from the DEP-FFF fractionator approximately 2–5 minutes after the initiation of fluid flow. Frequencies from 10 kHz to 500 kHz, voltages from 0.5 V p—p to 3 V p—p, and carrier fluid conductivities from 5–1000 mS/m may be used.

Cell Tracking

Cell fractionation, isolation, concentration and bursting may be investigated in the integrated devices. Cultured breast tumor cells may be mixed with PBMCs to provide a well-characterized and reproducible model system for investigating the performance and optimal operating conditions for the component parts of the integrated system. To assist in tracking the cell subpopulations, one may initially prelabel the breast cancer cells to facilitate tracking. This may be done in two ways. Initially, cells may be incubation for 10 mins in 25 $\mu$g/ml BCECF-AM (Molecular Probes), a fluorescein probe that is irreversibly accumulated by cells through the action of nonspecific esterases. BCECF is only accumulated by viable cells and simultaneously acts as a viability indicator. In experiments, such labeling allowed convenient tracking of tumor cells which appeared as brilliant spheres against a dark field of unlabelled cells, allowing even a single tumor cell within a very large unlabelled population (>$10^5$ cells) to be instantly identified. This tracking technique may be used to study the cells by fluorescent microscopy while they are undergoing separation and manipulations in the device.

Secondly, FITC-conjugated human epithelial antigen (HEA) antibody may be used to prelabel breast cancer cells prior to adding them to PBMNC mixtures. The fluorescence of this labeling procedure is much weaker than BCECF, however cells emerging from the separator stages can be passed directly into a flow cytometer and definitively identified as being of epithelial origin by this method.

Cell and cell culture: For model studies, one may use MDA-MB-435, MDA-MB-453, MDA-MB-236, and MDA-MB-468 human breast cancer lines originally established by Cailleau et al. as well as MCF-7 originally from the Michigan Cancer Foundation. These have formed the basis for investigations into many aspects of tumorogenesis and metastasis, are well characterized, and are available from ATTC to other researchers for follow-up studies. MDA-MB-453 shows a 64-fold enhancement in mRNA level of HER2/neu compared with MDA-MB-231 and a comparable increase in cell surface concentration of the corresponding protein and is therefore suitable for both immunological and mRNA assays. Tumor cells are cultured in RPMI 1640 medium supplemented with 10% fetal bovine serum, 1 mM glutamine and 20 mM HEPES buffer in 25-cm$^2$ vented culture flasks (Costar) at 37° C. under a 5% $CO_2$/95% air atmosphere. Cultures are free of, and are periodically checked by radionucleic acid hybridization assay (Gen-Probe, Inc.) for, mycoplasma. Cells are harvested from 50–70% confluent cultures by brief exposure to 0.25% trypsin-0.02% EDTA solution. Viability is determined by trypan blue dye exclusion.

Samples for DEP fractionation and manipulation may be prepared by suspending cells in sucrose/dextrose solution to yield suspensions having a specified conductivity of between 10 and 1000 mS/m and physiological osmolarity (300 mOs/kg). If necessary, conductivity is adjusted with additional culture medium.

Immunological Detection

Cell samples can be incubated with antibodies for markers prior to loading into the separation stages, while at the interface between the prefilter and DEP-MAP-FFF fractionator stages, and after trapping in the spiral electrode isolator stage prior to concentration. A series of DEP levitation/trapping cycles can be applied to "stir" the antibody/cell mixture at each of these steps. Following labeling, cells may be trapped by positive DEP and washed free of antibodies by perfusing them with rinsing reagents as many times as needed. Fluorescently, magnetically or enzymically labeled antibodies can be used. Fluorescence microscopy can be used to detect fluorescence of the antibodies or of their catalytic by-products. Immunomagnetic labels may modify the DEP-MAP-FFF properties of cell types in accordance with their surface marker concentrations. One may use antibodies for human epithelial antigen (HEA) because this is a useful marker for identifying epithelial cells in blood and lymph node cell dispersions, and EGF receptor antibody since this is a relevant prognostic marker for breast cancer. Clearly, these examples are merely exemplary of the more general applicability of the technology and surface markers relevant to any different application could be used instead.

twDEP Focusing/Concentration of Cells

The twDEP properties of blood and cultured breast cancer cell lines are known in the art. A traveling wave field applied to the spiral electrode array at a frequency that both levitates and translates a cell subpopulation may allow it to be focused at the center of the spiral. A swept frequency may be applied to ensure that all cell and bead types on each spiral isolation segment may be swept to the center to form a highly concentrated mixture. Traveling waves in the frequency range 10 kHz to 500 kHz, voltages from 0.5 V p—p to 5 V p—p, and carrier fluid conductivities from 5–1000 mS/m may be used.

Computer Control

In one embodiment, the pumps and signal generators used to operate the system are all computer controllable. Image processing may use a dual-Pentium II PCI/EISA mother board. The image grabber may include a real-time image processor (Image Series 640+Neighborhood Processor with on-board 4 MB memory, Matrox Electronic Systems Ltd., Dorval, Canada) that is used to acquire images and to accelerate image operations. Appropriate software known in the art performs real-time process control of the serial and HPIB devices (pumps, valves, signal sources, digital camera) used to operate the system and a real-time imaging library (MIL-32 3.10, Matrox Electronic Systems Ltd., Dorval, Canada) used in conjunction with Labview software may be exploited for system control and fluorescence detection.

Bursting of Cells

Following the trapping of cell fractions on the spiral electrode segments and their concentration by twDEP, the voltage and frequency applied to the spiral electrode may be changed to burst the target cells. A further level of cell discrimination is possible at this stage because targeted bursting can be done on cell mixtures if desired. Breast cancer cells are typically in the 10–12 $\mu$m diameter range and have specific membrane capacitances of ~20 mF/m$^2$. These parameters in conjunction with the suspending medium conductivity define the optimum bursting conditions. These may be examined for target cultured breast cancer and human specimen cells for carrier fluid conductivities from 5–1000 mS/m. Optimum field conditions for rapidly bursting all cells on the spiral electrode may also be determined. Voltages from 10 V peak—peak to 20V peak—peak and frequencies from 10 kHz to 100 kHz may be used, including swept frequencies.

While the present disclosure may be adaptable to various modifications and alternative forms, specific embodiments have been shown by way of example and described herein. However, it should be understood that the present disclosure is not intended to be limited to the particular forms disclosed. Rather, it is to cover all modifications, equivalents, and alternatives falling within the spirit and scope of the disclosure as defined by the appended claims. Moreover, the different aspects of the disclosed apparatus and methods may be utilized in various combinations and/or independently. Thus the invention is not limited to only those combinations shown herein, but rather may include other combinations.

EXAMPLE 3

Programmable Fluidic Processor

In one embodiment of the present invention, a programmable fluidic processor (PFP) may be coupled to the array isolator that may coupled to the electrode array isolator that is used to trap cells after they exit from the field-flow fractionation separator. Various embodiments of the PFP are discussed in pending U.S. application Ser. No. 09/249,955, which has been previously incorporated herein by reference.

As previously indicated, the array isolator may consist of a plurality of spiral traps. The PFP may be coupled to the spiral traps by a variety of means known in the art. For example, the PFP may be coupled to the spiral traps by means of a channel, or the PFP may be integral with the spiral traps. There may be one or more PFPs. Each spiral trap may have its own PFP, or multiple spiral traps may be connected to a single PFP.

Figure 12:
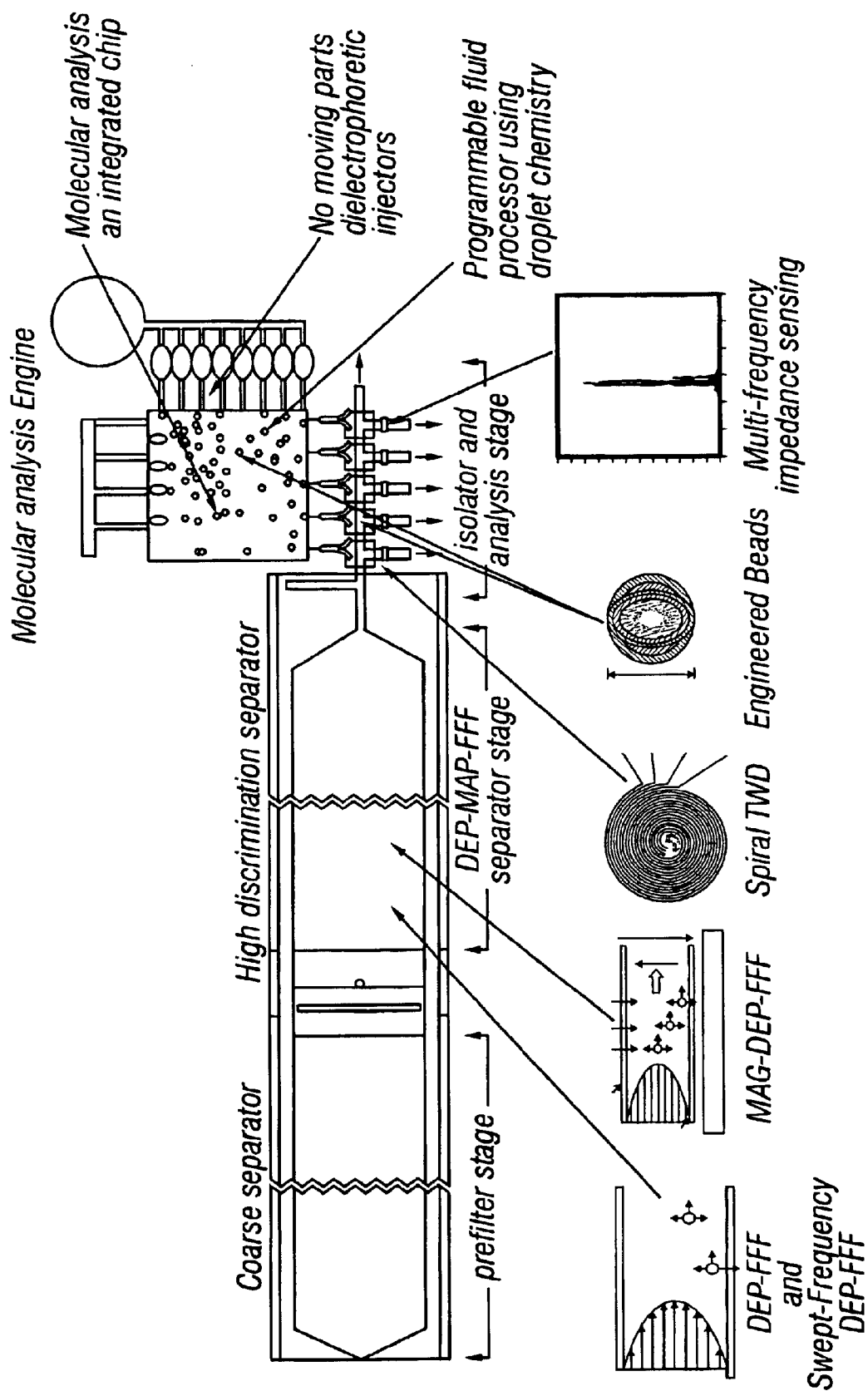
FIG. 12 is a schematic of one embodiment of the integrated fluidic system, including a prefilter stage, a separator stage, and an isolator and analysis stage that includes a programmable fluidic processor.

Once the cells have been trapped on the spiral traps, they may be moved to the PFP for further analysis. Once the cells have been transferred, the PFP may be used to programmably manipulate the cells in a variety of ways. FIG. 12 shows one embodiment of the present invention that includes a PFP. As shown in FIG. 12, a single PFP may be connected to each of the spiral traps.

REFERENCES

The following references are specifically incorporated herein by reference.

1. Reyes-Engel, A. and Dieguez-Lucena, J. L. (1993) Direct quantification of specific mRNA using a selected biotinylated oligonucleotide by free solution capillary electrophoresis. Nucleic Acids Research 21:(3), 759–760.
2. Muir, P., Nicholson, F. Jhetam, M., Neogi, S. and Banatvala, J. E. (1993) Rapid diagnosis of enterovirus infection by magnetic bead extraction and polymerase chain reaction detection of enterovirus RNA in clinical specimens. J. of Clinical Microbiology, 31(1) 31–38.
3. Krogh, T. N., Berg, T. and Hojrup, P. (1999) Protein analysis using enzymes immobilized to paramagnetic beads. Analytical Biochemistry, 274: 153–162.
4. Chalmers, J. L., et al., (1998) Quantification of cellular properties from external fields and resulting induced velocity: cellular hydrodynamic diameter. BB., 217: 1–19.
5. Zborowski, M., Sun, L., Moore, L. R., Williams, P. S. and Chalmers, J. J. (1999) Continuous cell separation using novel magnetic quadrupole flow sorter. J. Mag. & Mag. Materials, 194: 224–230.
6. Gascoyne, P. R. C., Huang, Y., Pethig, R., Vykoukal, J. and Becker F. F. (1992) Dielectrophoretic separation of mammalian cells studied by computerized image analysis Meas. Sci. Technol. 3:439–445.
7. Gascoyne, P. R. C., Pethig, R., Burt, J. P. H. and Becker, F. F. (1993) Membrane changes accompanying induced differentiation of murine erythroleukemia cells studied by dielectrophoresis. Biochim. Biophys. Acta 1149, 119–126.
8. Gascoyne, P. R. C., Noshari, J., Becker, F. F. and Pethig, R. (1994) Use of dielectrophoretic collection spectra for characterizing differences between normal and cancerous cells. IEEE. Trans. Ind. Appl. 30, 829–834.
9. Gascoyne, P. R. C., Wang, X-B. and Becker, F. F. (1995) Numerical analysis of the influence of experimental conditions on the accuracy of dielectric parameters derived from electrorotation measurements. Bioelectrochem. Bioenergetics, 36:115–125.
10. Huang, Y. and Pethig, R. (1991) Electrode design for negative dielectrophoresis. Meas. Sci. Technol. 2:1142–1146.
11. Huang, Y., (1994) A.C. Electrokinetics of Colloidal Particles, Ph.D Thesis of University of Wales, Bangor, UK Chapter 3, 47–70.
12. Hughes, M. P., Wang, X-B., Becker, F. F., Gascoyne, P. R. C. and Pethig, R. Computer-aided analysis of electric fields used in electrorotation studies. J. Phys. D: Appl. Phys. 27:1564–1570.
13. Gascoyne, P. R. C., Huang, Y., Hughes, M. P., Wang, X-B., Pethig, R. and Becker, F. F., (1994) Manipulations of biological cells using travelling-wave dielectrophoresis. Proc. 16th IEEE: Eng. Med. Biol. Soc. 772–773.
14. Wang, X-B., Huang, Y., Becker, F. F., and Gascoyne, P. R. C. (1994) A unified theory of dielectrophoresis and travelling wave dielectrophoresis. J. Phys. D: Appl. Phys. 27:1571–1574.

15. Wang, X.-B., Hughes, M. P., Huang, Y., Becker, F. F. and Gascoyne, P. R. C., (1995) Non-uniform distributions of magnitude and phase of AC electric fields determine dielectrophoretic forces. Biochim. Biophys. Acta. 1243:185–194.
16. Wang, X-B, Huang, Y., Gascoyne, P. R. C. and Becker F. F. (1994) Particle dipole—dipole interactions in A.C. electric fields. Proc. 16th IEEE: Eng. Med. Biol. Soc. 774–775.
17. Gascoyne, P. R. C., Huang, Y., Pethig, R., Vykoukal, J. and Becker F. F. (1992) Dielectrophoretic separation of mammalian cells studied by computerized image analysis Meas. Sci. Technol. 3:439–445.
18. Gascoyne, P. R. C., Pethig, R., Burt, J. P. H. and Becker, F. F. (1993) Membrane changes accompanying induced differentiation of murine erythroleukemia cells studied by dielectrophoresis. Biochim. Biophys. Acta 1149, 119–126.
19. Gascoyne, P. R. C., Noshari, J., Becker, F. F. and Pethig, R. (1994) Use of dielectrophoretic collection spectra for characterizing differences between normal and cancerous cells. IEEE. Trans. Ind. Appl. 30, 829–834.
20. Wang, X.-B., Huang, Y., Gascoyne, P. R. C., Becker F. F., Hölzel, R. and Pethig, R. (1994) Changes in Friend murine erythroleukaemia cell membranes during induced differentiation determined by electrorotation. Biochim. Biophys. Acta. 1193:330–344.
21. Huang, Y., Wang, X-B., Hölzel, R., Becker, F. F. and Gascoyne, P. R. C. (1995) Electrorotational studies of the cytoplasmic dielectric properties of Friend murine erythroleukaemia cells. Phys. Med. Biol. 40:1789–1806.
22. Becker, F. F., Wang, X-B., Huang, Y., Pethig, R., Vykoukal, J. and Gascoyne, P. R. C. (1995) Separation of human breast cancer cells from blood by differential dielectric affinity. Proc. Natl. Acad. Sci. USA. 29:860–864.
23. Becker, F. F., Wang, X-B., Huang, Y., Pethig, R., Vykoukal, J. and Gascoyne, P. R. C. (1994) The removal of human leukemia cells from blood using interdigitated microelectrodes. J. Phys. D: Appl. Phys. 27(12): 2659–2662.
24. Wang, X.-B., Huang, Y., Wang, X., Becker, F. F. and Gascoyne, P. R. C. (1997) Dielectrophoretic manipulation of cells with spiral electrodes. Biophys. J. 72:1887–1899.
25. Huang, Y., Wang, X-B., Becker, F. F. and Gascoyne, P. R. C. (1997) Introducing dielectrophoresis as a new force field for field-flow fractionation. Biophys. J. 73:1118–1129.
26. Wang, X-B., Vykoukal, J., Becker, F. F. and Gascoyne, P. R. C. (1998) Separation of polystyrene microbeads using dielectrophoretic/gravitational field-flow-fractionation. Biophys. J. 74:2689–2701.
27. Yang, J., Huang, Y., Wang, X-B., Becker, F. F. and Gascoyne, P. R. C. (1999) Cell separation on microfabricated electrodes using dielectrophoretic/gravitational field-flow fractionation. Analytical Chem., 71(5): 911–918.
28. Huang, Y., Yang, J., Wang, X-B., Becker, F. F. and Gascoyne, P. R. C. (1999) Cutting Edge Communication: the removal of human breast cancer cells from hematopoietic CD34+ stem cells by dielectrophoretic field-flow-fractionation. J. of Hematotherapy & Stem Cell Research, 8(5): 481–490.
29. De Gasperis, G., Yang, J., Becker, F. F., Gascoyne, P. R. C. and Wang, X-B., (1999) Microfluidic cell separation by 2-D dielectrophoresis, Biomedical Microdevices, 2:11, 41–49.
30. Wang, X., Wang, X-B. and Gascoyne, P. R. C. (1997) General expressions for dielectrophoretic force and electrorotational torque derived using the Maxwell stress tensor method. J. of Electrostatics. 39:277–295.
31. Huang, Y., Hölzel, R., Pethig, R. and Wang, X.-B. (1992) Differences in the AC electrodynamics of viable and non-viable yeast cells determined through dielectrophoresis and electrorotation studies. Phys. Med. Biol. 37:1499–1517.
32. Jones, T. B. and Kallio, G. A. (1979) Dielectrophoretic levitation of spheres and shells. J. Electrostat. 6:207–224.
33. Pohl, H. A. (1978) Dielectrophoresis (Cambridge University Press, Cambridge).
34. Huang, Y., Wang, X-B, Tame, J. A., and Pethig, R., (1993) Electrokinetic behaviour of colloidal particles in travelling electric fields: studies using yeast cells. J. Phys. D: Appl. Phys. 26:1528–1535.
35. Jones, T. B. and Kallio, G. A. (1979) Dielectrophoretic levitation of spheres and shells. J. Electrostat. 6:207–224.
36. Wang, X-B., Pethig, R. and Jones, T. B. (1992) Relationship of dielectrophoretic and electrorotational behaviour exhibited by polarized particles. J. Phys. D: Appl. Phys. 25:905–912.
37. Gascoyne, P. R. C., Wang, X-B., Huang, Y. and Becker, F. F. (1997) Dielectrophoretic separation of cancer cells from blood. IEEE Transactions on Industry Applications. 33(3):670–678.
38. Huang, Y., Wang, X-B., Becker, F. F. and Gascoyne, P. R. C. (1996) Membrane changes associated with the temperature-sensitive P85gas-mos-dependent transformation of rat kidney cells as determined by dielectrophoresis and electrorotation. Biochimica et Biophysica Acta. 1282:76–84.
39. Jones, T. B., (1995), Electromechanics of Particles: Dielectrophoresis and magnetophoresis (ch. 3), Cambridge University Press, NY., 34–82.
40. Zborowski, M., Bor Fuh, C., Green, R., Sun, L. and Chalmers, J. J. (1995) Analytical magnetapheresis of ferritin-labeled lymphocytes. Anal. Chem. 67, 3702–3712.
41. Wang, X.-B., Vykoukal, J., Becker, F. F. and Gascoyne, P. R. C. (1998) Separation of polystyrene microbeads using dielectrophoretic/gravitational field-flow-fractionation. Biophy. J., 74, 2689–2701.
42. Gascoyne, P. R. C., Wang, X-B., Vykoukal, J., Ackler, H., Swierkowski, S. and Krulevitch, P. (1998) A microfluidic device combining dielectrophoresis and field flow fractionation for particle and cell discrimination. Proceedings of Solid State Sensor and Actuator Workshop, Hilton Head Supplement, 37–38.
43. vet thing ac coulter style
44. Schechter A L, Hung M C, Vaidyanathan L, et al: (1985) The neu gene: an erbB-homologous gene distinct from and unlinked to the gene encoding the EGF receptor. Science 229: 976–978.
45. Bargmann C l, Hung M C, and Weinberg R A: (1986) The neu oncogene encodes an epidermal growth factor receptor-related protein. Nature 319: 226–230.
46. Bargmann C l, Hung M C, and Weinberg R A: (1986) Multiple independent activations of the neu oncogene by a point mutation altering the transmembrane domain of p185. Cell 45: 649–657.
47. Yu D H and Hung M C: (1991) Expression of the activated rat neu oncogene is sufficient to induce experimental metastasis in the 3T3 cells. Oncogene 6: 1991–1996.
48. McCann A H, Dervan P A, O'Regan M, et al: (1991) Prognostic signifigance of c-erB-2 and estrogen receptor status in human breast cancer. Cancer Res 51:3296–3303.

49. Slamon D J, Clark G M, Wong S G, et al: (1987) Human breast cancer: correlation of relapse and survival with amplification of the HER-2/neu oncogene. Science 235:177–182.
50. van de Vijver M, van de Bersselaar R, Devilee P, et al: (1987) Amplification of the neu (c-erB-2) oncogene in human mammary tumors is relatively frequent and is often accompanied by amplification of the linked c-erBA oncogene. Mol Cell Biol 7: 2019–2023.
51. Gusterson B A, Gelber R D, Goldhirsch A, et al: (1992) Prognostic importancfe of c-erB-2 expression in breast cancer. International (Ludwig) Breast Cancer Study Group. J Clin Oncol 10: 1049–1056.
52. Slamon D J, Godolphin W, Jones L A, et al: (1989) Studies of the HER-2/neu proto-oncogene in human breast and ovarian cancer. Science 244: 707–712.
53. Berchuck A, Kamel A, Whitaker R, et al: (1990) Overexpression of HER-2/neu is associated with poor survival in advanced epithelial ovarian cancer. Cancer Res 50: 4087–4091.
54. Zhang X, Silva E, Gershenson D, et al: (1989) Amplification and rearrangement of c-erb B proto-oncogenes in cancer of human female gential tract. Oncogene 4: 985–989.
55. Schneider P M, Hung M C, Chiocca S M, et al: (1989) Differential expression of the c-erB-2 gene in human small cell and non-small cell lung cancer. Cancer Res 49: 4968–4971.
56. Plowman, G. D., Whitney, G. S., Neubauer, M. G., Green, J. M., McDonald, V. L., Todaro, G. J., and Shoyab, M. (1990) Molecular cloning and expression of an additional epidermal growth factor receptor-related gene. Proc. Nat. Acad. Sci. USA, 87: 4905–4909.
57. Todaro, G. J., Rose, T. M., Spooner, C. E., Shoyab, M., and Plowman, G. D. Cellular and viral ligands that interact with the EGF receptor. Seminars in Cancer Biology, 1: 257–263, 1990.
58. Velu, T. J., Beguinot, L., Vass, W. C., Willingham, M. C., Merlino, G. T., Pastan, I., and Lowy, D. R. (1987) Epidermal-growth-factor-dependent transformation by a human EGF receptor proto-oncogene. Science, 238: 1408–10.
59. Di Fiore, P. P., Pierce, J. H., Fleming, T. P., Hazan, R., Ullrich, A., King, C. R., Schlessinger, J., and Aaronson, S. A. (1987) Overexpression of the human EGF receptor confers an EGF-dependent transformed phenotype to NIH 3T3 cells. Cell, 51: 1063–70.
60. Riedel, H., Massoglia, S., Schlessinger, J., and Ullrich, A. (1988) Ligand activation of overexpressed epidermal growth factor receptors transforms NIH 3T3 mouse fibroblasts. Proc. Nat. Acad. Sci. USA, 85: 1477–81.
61. Sainsbury, J. R., Farndon, J. R., Sherbet, G. V., and Harris, A. L. Epidermal-growth-factor receptors and oestrogen receptors in human breast cancer. Lancet, 1: 364–6, 1985.
62. Hendler, F. J. and Ozanne, B. W. (1984) Human squamous cell lung cancers express increased epidermal growth factor receptors. Journal of Clinical Investigation, 74: 647–51.
63. Rusch, V., Baselga, J., Cordon-Cardo, C., Orazem, J., Zaman, M., Hoda, S., McIntosh, J., Kurie, J., and Dmitrovsky, E. (1993) Differential expression of the epidermal growth factor receptor and its ligands in primary non-small cell lung cancers and adjacent benign lung. Cancer Res., 53: 2379–85.
64. Veale, D., Ashcroft, T., Marsh, C., Gibson, G. J., and Harris, A. L. (1987) Epidermal growth factor receptors in non-small cell lung cancer. Br. J. Cancer, 55: 513–6.
65. Humphrey, P. A., Wong, A. J., Vogelstein, B., Friedman, H. S., Werner, M. H., Bigner, D. D., and Bigner, S. H. (1988) Amplification and expression of the epidermal growth factor receptor gene in human glioma xenografts. Cancer Res., 48: 2231–8.
66. Eisbruch, A., Blick, M., Lee, J. S., Sacks, P. G., and Gutterman, J. (1987) Analysis of the epidermal growth factor receptor gene in fresh human head and neck tumors. Cancer Res., 47: 3603–5.
67. Neal, D. E., Marsh, C., Bennett, M. K., Abel, P. D., Hall, R. R., Sainsbury, J. R., and Harris, A. L. (1985) Epidermal-growth-factor receptors in human bladder cancer: comparison of invasive and superficial tumours. Lancet, 1: 366–8.
68. Sainsbury, J. R., Malcolm, A. J., Appleton, D. R., Farndon, J. R., and Harris, A. L. 1985, Presence of epidermal growth factor receptor as an indicator of poor prognosis in patients with breast cancer. Journal of Clinical Pathology, 38, 1225–8.
69. Holland, P. M., Abramson, R. D., Watson, R. and Gelfand, D. H. (1991) Detection of specific polymerase chain reaction products by utilizing 5'->3' exonuclease activity of Thermus aquaticus DNA polymerase. Proc. Natl. Acad. Sci. 88:7276–7280.
70. Prasad, K. A., and Church, J. G. (1997) EGF effects on p53 in MDA-468 human breast cancer cells. Cell Proliferation, 30: 81–94.
71. Xia, W., Lau, Y.-K., Zhang, H.-Z., Liu, A.-R., Kiyokawa, N., Clayman, G. L., Katz, R. L., and Hung, M.-C. (1997) Strong correlation between c-erbB-2 overexpression and overall survival of patients with oral squamous cell carcinoma. Clin. Cancer Res., 3: 3–9.

What is claimed is:

1. A fluidic device for the analysis of cells, the device comprising:
a dielectrophoretic field-flow fractionation separator configured to discriminate cells by balancing a dielectrophoretic force with a gravitational force to displace the cells to positions within a velocity profile in the separator; and
a multi-segment electrode array isolator coupled to the separator and configured to trap at least a portion of the cells emerging from the separator.

2. The fluidic device of claim 1, further comprising a dielectrophoretic prefilter coupled to the separator, the prefilter comprising one or more trapping electrodes configured to trap at least a portion of the cells with a dielectrophoretic force.

3. The fluidic device of claim 1, wherein the separator further comprises a magnet configured to displace with a matnetophoretic force the cells to positions within the velocity profile in the separator.

4. The fluidic device of claim 3, wherein the magnet comprises SnCo or NdFeB.

5. The fluidic device of claim 1, further comprising a programmable fluidic processor coupled to the electrode array isolator.

6. A fluidic device for the analysis of cells, the device comprising:
a dielectrophoretic prefilter comprising one or more trapping electrodes configured to trap at least a portion of the cells with a dielectrophoretic force;
a dielectrophoretic field-flow fractionation separator coupled to the prefilter and configured to discriminate cells by balancing a dielectrophoretic force with a gravitational force to displace the cells to positions within a velocity profile in the separator; and two or more spiral electrode segments coupled to the separator and configured to trap at least a portion of the cells as a function of the cells' time of emergence from the separator.

7. The fluidic device of claim 6, wherein the two or more spiral electrode segments each comprise a plurality of electrode elements, wherein each of the plurality of electrode elements are configured to be energized by a signal of a single frequency, but wherein the phase of the signal is different for each of the plurality of electrode elements.

8. The fluidic device of claim 7, said plurality of electrode elements comprising four electrode elements, and wherein the phases of the signal are 0°, 90°, 180°, 270°.

9. The fluidic device of claim 6, further comprising a reagent port configured to allow for the injection of reagents onto the cells trapped on the spiral electrode segments.

10. The fluidic device of claim 6, wherein the separator further comprises a magnet configured to displace with a matnetophoretic force the cells to positions within a velocity profile in the separator.

11. The fluidic device of claim 10, further comprising a programmable fluidic processor coupled to the two or more spiral electrode segments.

12. A fluidic device for the analysis of cells, the device comprising:
a dielectrophoretic field-flow fractionation separator configured to discriminate cells by balancing a dielectrophoretic force with a gravitational force to displace the cells to positions within a velocity profile in the separator;
a multi-segment electrode array isolator coupled to the separator and configured to trap at least a portion of the cells emerging from the separator; and
a programmable fluidic processor coupled to the electrode array isolator.

13. The fluidic device of claim 12, further comprising a dielectrophoretic prefilter coupled to the separator, the prefilter comprising one or more trapping electrodes configured to trap at least a portion of the cells with a dielectrophoretic force.

14. The fluidic device of claim 12, wherein the separator further comprises a magnet configured to displace with a matnetophoretic force the cells to positions within a velocity profile in the separator.

15. A method for cell isolation and analysis, comprising:
introducing cells into a dielectrophoretic field-flow fractionation separator;
discriminating the cells in the separator, the discriminating comprising balancing a dielectrophoretic force with a gravitational force to displace the cells to positions within a velocity profile in the separator; and
trapping at least a portion of the cells emerging from the separator with a multi-segment electrode array isolator coupled to the separator.

16. The method of claim 15 wherein at least a portion of the cells are initially coupled to the surface of a carrier bead.

17. The method of claim 15 wherein the step of discriminating the cells further comprises using a magnetophoretic force to displace the cells to positions within a velocity profile in the separator.

18. The method of claim 17, wherein the cells are incubated with magnetically labeled antibodies.

19. The method of claim 15, further comprising lysing the cells trapped by the multu-segment electrode array isolator.

20. The method of claim 19 wherein the lysing comprises using AC electrical fields.

21. The method of claim 15, further comprising introducing cells into a dielectrophoretic prefilter comprising one or more trapping electrodes configured to trap at least a portion of the cells.

22. The method of claim 15, further comprising manipulating the cells using a programmable fluidic processor coupled to the multi-segment electrode array isolator.

23. A method for cell isolation and analysis, comprising:
introducing cells into a dielectrophoretic prefilter comprising one or more trapping electrodes configured to trap at least a portion of the cells with a dielectrophoretic force;
directing the cells trapped from the prefilter into a dielectrophoretic field-flow fractionation separator coupled to the prefilter;
discriminating the cells, the discriminating comprising balancing a dielectrophoretic force with a gravitational force to displace the cells to positions within a velocity profile in the separator; and
trapping at least a portion of the cells as a function of the cells' time of emergence from the separator with two or more spiral electrode segments coupled to the separator.

24. The method of claim 23 wherein the step of discriminating the cells further comprises using a magnetophoretic force to displace the cells to positions within a velocity profile in the separator.

25. The method of claim 24, wherein the cells are incubated with magnetically labeled antibodies.

26. The method of claim 23, wherein a plurality of analysis beads are mixed with the cells after the cells emerge from the separator.

27. The method of claim 23, further comprising concentrating the cells on the two or more spiral electrode segments, the concentrating comprising energizing the two or more electrode segments with a multi-phase field.

28. The method of claim 27, wherein the multi-phase field comprises four phases, and comprises a frequency between 10 KHz to 200 kHz.

29. The method of claim 23, further comprising manipulating the cells with a programmable fluidic processor coupled to the two or more spiral electrode segments.

30. A method for cell isolation and analysis, comprising:
introducing cells into a dielectrophoretic field-flow fractionation separator;
discriminating the cells in the separator, the discriminating comprising balancing a dielectrophoretic force with a gravitational force to displace the cells to positions within a velocity profile in the separator;
trapping at least a portion of the cells emerging from the separator with a multi-segment electrode array isolator coupled to the separator;
manipulating the cells with a programmable fluidic processor coupled to the electrode array isolator.

31. The method of claim 30 wherein the step of discriminating the cells further comprises using a magnetophoretic force to displace the cells to positions within a velocity profile in the separator.

32. The method of claim 30, further comprising introducing cells into a dielectrophoretic prefilter comprising one or more trapping electrodes configured to trap at least a portion of the cells.

* * * * *

UNITED STATES PATENT AND TRADEMARK OFFICE
CERTIFICATE OF CORRECTION

PATENT NO. : 6,790,330 B2
DATED : September 14, 2004
INVENTOR(S) : Gascoyne et al.

It is certified that error appears in the above-identified patent and that said Letters Patent is hereby corrected as shown below:

Column 28,
Line 51, please delete "matnetophoretic" and insert -- magnetophoretic --.

Column 29,
Lines 19 and 45, please delete "matnetophoretic" and insert -- magnetophoretic --.
Line 65, please delete "multu-segment" and insert -- multi-segment --.

Column 30,
Line 55, after "separator;" please insert -- and --.

Signed and Sealed this

Sixteenth Day of August, 2005

JON W. DUDAS
*Director of the United States Patent and Trademark Office*